US009709571B2

(12) United States Patent
Tometzki et al.

(10) Patent No.: US 9,709,571 B2
(45) Date of Patent: *Jul. 18, 2017

(54) METHOD OF DRUG DESIGN

(71) Applicants:Michael L. West, Eight Mile Plains (AU); VAST BIOSCIENCE PTY LIMITED, St Lucia (AU)

(72) Inventors: Gerald B. Tometzki, Manly West (AU); Wim F. Meutermans, Toowong (AU); Johannes Zuegg, Wynnum (AU)

(73) Assignee: VAST BIOSCIENCE PTY LIMITED, St. Lucia (AU)

( * ) Notice: Subject to any disclaimer, the term of this patent is extended or adjusted under 35 U.S.C. 154(b) by 1186 days.

This patent is subject to a terminal disclaimer.

(21) Appl. No.: 13/772,222

(22) Filed: Feb. 20, 2013

(65) Prior Publication Data

US 2013/0172210 A1 Jul. 4, 2013

Related U.S. Application Data

(63) Continuation of application No. 12/063,920, filed as application No. PCT/AU2006/001431 on Oct. 3, 2006, now Pat. No. 8,426,345.

(30) Foreign Application Priority Data

Oct. 4, 2005 (AU) ................................ 2005905465

(51) Int. Cl.
*C07H 3/02* (2006.01)
*G01N 33/68* (2006.01)
*C07H 15/18* (2006.01)
*G01N 33/566* (2006.01)

(52) U.S. Cl.
CPC ............... *G01N 33/68* (2013.01); *C07H 3/02* (2013.01); *C07H 15/18* (2013.01); *G01N 33/566* (2013.01); *G01N 2333/726* (2013.01); *G01N 2500/04* (2013.01)

(58) Field of Classification Search
None
See application file for complete search history.

(56) References Cited

U.S. PATENT DOCUMENTS

| 2002/0115107 A1 | 8/2002 | Ellman et al. |
| 2003/0186850 A1 | 10/2003 | Clausen et al. |
| 2004/0077826 A1 | 4/2004 | Koganty et al. |
| 2005/0245746 A1 | 11/2005 | Meutermans et al. |
| 2006/0223764 A1 | 10/2006 | Meutermans et al. |
| 2009/0163373 A1 | 6/2009 | Tometzki et al. |

FOREIGN PATENT DOCUMENTS

| WO | WO-95/18971 A1 | 7/1995 |
| WO | WO-97/34623 A1 | 9/1997 |
| WO | WO-03/082846 A1 | 10/2003 |
| WO | WO-2004/014929 A1 | 2/2004 |
| WO | WO-2004/022572 A1 | 3/2004 |
| WO | WO-2004/032940 A1 | 4/2004 |
| WO | WO-2005/097142 A1 | 10/2005 |

OTHER PUBLICATIONS

Lin et al (2004 JACS 126:13998-14003).*
Achkar, J. et al (2005). "Synthesis and Conformational Analysis of 6-C-Methyl-Substituted 2-Acetamido-2-deoxy-β-D-glucopyranosyl Mono- and Disaccharides," *Journal of Organic Chemistry* 70(1):214-226.
Ando, H. et al. (2001). "Solid-Phase Capture-Release Strategy Applied to Oligosaccharide Synthesis on a Soluble Polymer Support," *Angew. Chem. Int. Ed.* 40(24):4725-4728.
Bauer, W. et al. (1982). "SMS201-995: A Very Potent and Selective Octapeptide Analogue of Somatostatin with Prolonged Action," *Life Sciences* 31:1133-1140.
Creswell, M.W. et al. (1998). "Combinatorial Synthesis of Dihydropyridone Libraries and their Derivatives," *Tetrahedron* 54:3983-3998.
Csaba, Z. et al. (2001). "Cellular Biology of Somatostatin Receptors," *Neuropeptides* 35(1):1-23.
Database Caplus on CAN, Acc. No. 127:293557, Sofia, M. et al. (Sep. 25, 1997). "Combinatorial Library and Solid-Phase Preparation of Lipoglycopeptides as Bactericides," WO 1997/034623 (abstract).
Database Caplus on CAN, Acc. No. 136:263346, Ando, H. et al. (2001). "Solid-Phase Capture-Release Strategy Applied to Oligosaccharide Synthesis on a Soluble Polymer Support," *Angewandte Chemie, Intl. Ed.* 40(24), pp. 4725-4728 (abstract).
Database Caplus on CAN, Acc. No. 141:411151, Hernandez-Torres, J.M. et al. (2004). "Temperature-Controlled Regioselectivity in the Reductive Cleavage of p-Methoxybenzylidene Acetals," *Journal of Organic Chemistry* 69(21), pp. 7206-7211 (abstract).
Database Caplus on CAN, Acc. 142:156241, Achkar, J. et al. (2005). "Synthesis and Conformational Analysis of 6-C-Methyl-Substituted 2-Acetamido-2-deoxy-β-D-glucopyranosyl Mono- and Disaccharides," *Journal of Organic Chemistry* 70(1), pp. 214-226 (abstract).
Ghosh et al. (2000). "Efficient Synthesis of a Stereochemically Defined Carbohydrate Scaffold: Carboxymethyl 2_Acetamido-6-Azido_4-O-Benzyl-2-deoxy-α-D-Glucopyranoside," *JOC* 65:8387-8390.
Hernandez-Torres, J.M. et al. (2004). "Temperature-Controlled Regioselectivity in the Reductive Cleavage of p-Methoxybenzylidene Acetals," *Journal of Organic Chemistry* 69(21):7206-7211.

(Continued)

*Primary Examiner* — Christopher M Gross
(74) *Attorney, Agent, or Firm* — Morrison & Foerster LLP

(57) ABSTRACT

The invention provides a method of identifying biologically active compounds comprising: (a) designing a first library of compounds of formula (1) to scan molecular diversity wherein each compound of the library has at least two pharmacophoric groups R1 to R5 as defined below and wherein compound of the library has same number of pharmacophoric groups; (b) assaying the first library of compounds in one or more biological assay(s); and (c) designing a second library wherein each compound of the second library contains one or more additional pharmacophoric group with respect to the first library; such that the/each component of the first and second library is a compound of formula (1).

21 Claims, No Drawings

(56) References Cited

OTHER PUBLICATIONS

Hirschmann, R. et al. (1998). "Modulation of Receptor and Receptor Subtype Affinities Using Diastereomeric and Enantiomeric Monosaccharide Scaffolds as a Means to Structural and Biological Diversity. A New Route to Ether Synthesis," *J. Med. Chem.* 41(9):1382-1391.

International Search Report mailed on Feb. 2, 2007, for PCT Application No. PCT/AU2006/001431, filed on Oct. 3, 2006, 6 pages.

Jain, R. et al. (2003). "3-Azido-3-deoxy-glycopyranoside Derivatives as Scaffolds for the Synthesis of Carbohydrate-Based Universal Pharmacophore Mapping Libraries," *Bioorganic & Medicinal Chemistry Letters* 13(13):2185-2189.

Lamberts, S.W.J. et al. (Jan. 25, 1996). "Drug Therapy: Octreotide," *N. Eng. J. Med.* 334(4):246-254.

Le, G.T. et al. (Aug. 2003). "Molecular Diversity through Sugar Scaffolds," *Drug Discovery Today* 8(15):701-709.

Le Digauher, T. et al. (1996). "Syntheis of Potential Peptidomimetics Based on Highly Substituted Glucose and Allose Scaffolds," *Bioorganic & Medicinal Chemistry Letters* 6(16):1983-1988.

Patel, Y.C. (1999). "Somatostatin and its Receptor Family," *Frontiers in Neuroendocrinology* 20:157-198.

Reisine, T. (1995). "Somatostatin Receptors," *Am. J. Physiol.* 269:G813-G820.

Reisine, T. et al. (1995). "Molecular Biology of Somatostatin Receptors," *Endocr. Rev.* 16(4):427-442.

Robinson, C. et al. (1994). "Lanreotide Acetate," *Drugs Future* 19(11):992-999.

Vetter, D. et al. (1995). "Strategies for the Syntheis and Screening of Glycoconjugates. 1. A Library of Glycosylamines," *Bioconjugate Chem.* 6:316-318.

\* cited by examiner

METHOD OF DRUG DESIGN

CROSS-REFERENCE TO RELATED APPLICATIONS

This application is a continuation of U.S. patent application Ser. No. 12/063,920, now U.S. Pat. No. 8,426,345, filed Jun. 19, 2008, which is a National Phase application under 35 U.S.C. §371 of International Application No. PCT/AU2006/001431, filed Oct. 3, 2006 and claims the benefit of Australian Application No. 2005905465, filed Oct. 4, 2005, the disclosures of which are incorporated herein by reference in their entirety.

FIELD OF THE INVENTION

The invention relates to a method of identifying biologically active compounds, libraries of compounds.

BACKGROUND

Small molecules involved in molecular interactions with a therapeutic target, be it enzyme or receptor, are often described in terms of binding elements or pharmacophoric groups which directly interact with the target, and non-binding components which form the framework of the bioactive molecule. In the case of peptide ligands or substrates for instance, usually a number of amino add side chains form direct interactions with their receptor or enzyme, whereas specific folds of the peptide backbone (and other amino acid residues) provide the structure or scaffold that controls the relative positioning of these side chains. In other words, the three dimensional structure of the peptide serves to present specific side chains in the required fashion suitable for binding to a therapeutic target. The problem is that such models do not allow for rapid identification of drug candidates owing to the necessity to synthesize an enormous amount of compounds to identify potential active compounds.

A pharmacophoric group in the context of these libraries is an appended group or substituent, or part thereof, which imparts pharmacological activity to the molecule.

Molecular diversity could be considered as consisting of diversity in pharmacophoric group combinations (diversity in substituents) and diversity in the way these pharmacophoric groups are presented (diversity in shape). Libraries of compounds in which either diversity of substituents, or diversity of shape, or both of these parameters are varied systematically are said to scan molecular diversity.

Carbohydrate scaffolds provide a unique opportunity to create libraries of structurally diverse molecules, by varying the pharmacophoric groups, the scaffold and the positions of attachment of the pharmacophoric groups in a systematic manner. Such diversity libraries allow the rapid identification of minimal components or fragments containing at least two pharmacophoric groups required for an interaction with a biological target. These fragments can be further optimized to provide potent molecules for drug design. Therefore these types of carbohydrate libraries provide an excellent basis for scanning molecular diversity.

In previous applications (WO2004014929 and WO2003082846) we demonstrated that arrays of novel compounds could be synthesized in a combinatorial manner. The libraries of molecules described in these inventions were synthesized in a manner such that the position, orientation and chemical characteristics of pharmacophoric groups around a range of chemical scaffolds, could be modified and/or controlled. These applications demonstrate the synthesis and biological activity of a number of new chemical entities.

Many drug discovery strategies fall owing to lack of knowledge of the bioactive conformation of, or the inability to successfully mimic the bioactive conformation of the natural ligand for a receptor. Libraries of compounds of the present invention allow for the systematic "scanning" of conformational space to identify the bioactive conformation of the target.

Typically in the prior art, libraries based on molecular diversity are generated in a random rather than a systematic manner. This type of random approach requires large number of compounds to be included in the library to scan for molecular diversity. Further, this approach may also result in gaps in the model because of not effectively accessing all available molecular space.

Therefore, one of the problems in the prior art is the necessity to synthesize an enormous amount of compounds to identify potential active compounds. Attempts have been made to develop peptidomimetics using sugar scaffolds by Sofia et al. (*Bioorganic & Medicinal Chemistry Letters* (2003) 13, 2185-2189). Sofia describes the synthesis of monosaccharide scaffolds, specifically containing a carboxylic acid group, a masked amino group ($N_3$) and a hydroxyl group as substitution points on the scaffold, with the two remaining hydroxyl groups being converted to their methyl ethers. Sofia teaches a specific subset of scaffolds not encompassed by the present invention and does not contemplate methods to simplify the optimization of pharmacophoric groups.

Therefore there remains a need to provide a method of effectively scanning libraries designed from compounds with a wider range of different pharmacophoric groups.

The present invention is directed to a method of drug design utilizing iterative scanning libraries, resulting in surprisingly efficient identification of drug candidates, starting from a selected number of pharmacophores (e.g., two) in the first library and designing subsequent libraries with additional pharmacophores based on SAR information from the first library.

The invention can provide a new method for the rapid identification of active molecules.

In an embodiment, and to demonstrate the versatility of our invention, one of the G-protein coupled receptors (GP-CR's) was chosen as a target the somatostatin receptor (SST receptor). The tetradecapeptide somatostatin is widely distributed in the endocrine and exocrine system, where it has an essential role in regulating hormone secretion [1-3]. Five different subtypes have been identified to date (SST1-5), which are expressed in varying ratios throughout different tissues in the body. Somatostatin receptors are also expressed in tumours and peptide analogues of somatostatin affecting mainly SST5, such as octreotide, lanreotide, vapreotide and seglitide [4-7] have antiproliferative effects. They are used clinically for the treatment of hormone-producing pituitary, pancreatic, and intestinal tumours. SST5 is also implicated in angiogenesis, opening up the possibility of developing anti-angiogenic drugs that act on the SST5 receptor, for example for the use in oncology. The "core sequence" in somatostatin responsible for its biological activity is Phe-Trp-Lys (FWK), representing a motif of two aromatic groups and a positive charge, which is found in almost all SST receptor active compounds.

It will be clearly understood that, if a prior art publication is referred to herein, this reference does not constitute an admission that the publication forms part of the common general knowledge in the art in Australia or in any other country.

SUMMARY OF THE INVENTION

In one form, the invention provides a method of identifying biologically active compounds comprising:
(a) designing a first library of compounds of formula 1 to scan molecular diversity wherein each compound of the library has at least two pharmacophoric groups R1 to R5 as defined below and wherein compound of the library has same number of pharmacophoric groups;
b) assaying the first library of compounds in one or more biological assay(s); and
(c) designing a second library wherein each compound of the second library contains one or more additional pharmacophoric group with respect to the first library;
such that the/each component of the first and second library is a compound of formula 1:

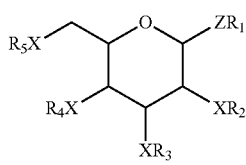

Formula 1 wherein the ring may be of any configuration;
Z is sulphur, oxygen, $CH_2$, $C(O)$, $C(O)NR^A$, NH, $NR^A$ or hydrogen, in the case where Z is hydrogen then $R_1$ is not present, $R^A$ is selected from the set defined for $R_1$ to $R_5$, or wherein Z and R1 together form a heterocycle,
X is oxygen or nitrogen providing that at least one X of Formula I is nitrogen, X may also combine independently with one of $R_1$ to $R_5$ to form an azide.
$R_1$ to $R_5$ are independently selected from the following nor groups H, methyl and acetyl, and pharmacophoric groups, $R_1$ to $R_5$ are independently selected from the group which includes but is not limited to $C_2$ to $C_{20}$ alkyl or acyl excluding acetyl; $C_2$ to $C_{20}$ alkenyl, all heteroalkyl; $C_2$ to $C_{20}$ aryl, heteroaryl, arylalkyl or heteroarylalkyl, which is optionally substituted, and can be branched or linear,
or wherein X and the corresponding R moiety, $R_2$ to $R_5$ respectively, combine to for a heterocycle.

In another form, the invention comprises biologically active compounds when identified by the method described above.

In a preferred embodiment, the invention relates to said method wherein in the first library, three of the substituents $R_1$-$R_5$ are non-pharmacophoric groups and are selected from hydrogen or methyl or acetyl.

In a preferred embodiment, the invention relates to said first method wherein in the first library, two of the substituents $R_1$-$R_5$ are non-pharmacophoric groups and are selected from hydrogen or methyl or acetyl.

In a preferred embodiment, the invention relates to said first method wherein Z is sulphur or oxygen;

In a preferred embodiment, the invention relates to said first method wherein at least one of the pharmacophoric groups is selected from aryl, arylalkyl, heteroaryl, heteroarylalkyl or acyl In a preferred embodiment, the invention relates to a library of compounds selected from compounds of formula 1 wherein in the first library, three of the non-pharmacophoric groups $R_1$-$R_5$ are hydrogen or methyl or acetyl when used according to said first method.

In a preferred embodiment, the invention relates to a library of compounds selected from compounds of formula 1 wherein in the second library, two of the non-pharmacophoric groups $R_1$-$R_5$ are hydrogen or methyl or acetyl when used according to said first method.

In a preferred embodiment, the invention relates to said first method wherein the/each component of the library is a compound selected from formula 2 or formula 3 or formula 4

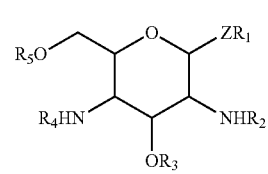

Formula 2

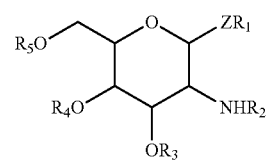

Formula 3

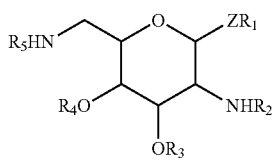

Formula 4

In a preferred embodiment, the invention relates to said first method wherein the/each component of the library is a compound selected from formula 2 or formula 3 or formula 4 and wherein the/each compound is of the gluco- or galacto- or allo-configuration.

In a preferred embodiment, the invention relates to said first method wherein the/each component of the library is a compound selected from formula 2 or formula 3 or formula 4 wherein the/each compound is of the galacto-configuration.

In a preferred embodiment, the invention relates to said first method wherein the/each component of the library is a compound selected from formula 2 or formula 3 or formula 4 and wherein the/each compound is of the gluco-configuration.

In a preferred embodiment, the invention relates to said first method wherein each component of the library is a compound selected from formula 2 or formula 3 or formula 4 and wherein the/each compound is of the allo-configuration.

In a preferred embodiment, the invention relates to said first method wherein designing the library comprises molecular modeling to assess molecular diversity.

In a preferred embodiment, the invention rebates to said first method wherein $R_1$ to $R_5$ optional substituents include OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, aminoaryl, aminoheteroaryl, thioalkyl, thioaryl or thioheteroaryl, which may optionally be further substituted.

The term "halogen" denotes fluorine, chlorine, bromine or iodine, preferably fluorine, chlorine or bromine.

The term "alkyl" used either alone or in compound words such as "optionally substituted alkyl", "optionally substituted cycloalkyl", "arylalkyl" or "heteroarylalkyl", denotes straight chain, branched or cyclic alkyl, preferably C1-20 alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 2-dimethylbutyl, 1,3-dimethylbutyl, 1,2,2trimethylpropyl, 1,2-trimethylpropyl, heptyl, 5-methylhexyl, 1-methylhexyl, 2,2-dimethylpentyl, 3,3dimethylpentyl, 4,4-dimethylpentyl, 1,2-dimethylpentyl, 1,3-dimethylpentyl, 1,4-dimethylpentyl, 1,2,3trimethylbutyl, 1,1,2-trimethylbutyl, 1,1,3-trimethylbutyl, octyl, 6-methylheptyl, 1-methylheptyl, 1,1,3,3tetramethylbutyl, nonyl, 1-, 2-, 3-, 4-, 5-, 6- or 7methyloctyl, 1-, 2-, 3-, 4- or 5-ethylheptyl, 1-, 2- or 3propylhexyl, decyl, 1-, 2-, 3-, 4-, 5-, 6-, 7- or 8-methylnonyl, 1-, 2-, 3-, 4-, 5- or 6-ethyloctyl, 1-, 2-, 3 or 4-propylheptyl, undecyl 1-, 2-, 3-, 4-, 5-, 6-, 7-, 8 or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2 pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

The term "alkylene" used either alone or in compound words such as "optionally substituted alkylenyl" denotes the same groups as "alkyl" defined above except that an additional hydrogen has been removed to form a divalent radical. It will be understood that the optional substituent may be attached to or form part of the alkylene chain.

The term "alkenyl" used either alone or in compound words such as "optionally substituted alkenyl" denotes groups formed from straight chain, branched or cyclic alkenes including ethylenically mono-, di- or polyunsaturated alkyl or cycloalkyl groups as defined above, preferably C2-6 alkenyl. Examples of alkenyl include vinyl, allyl, 1-methylvinyl, butenyl, iso-butenyl, 3-methyl-2butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1 decenyl, 3-decenyl, 1,3-butadienyl, 1,4-pentadienyl, 1,3 cyclopentadienyl, 1,3-hexadienyl, 1,4-hexadienyl, 1,3cyclohexadienyl, 1,4-cyclohexadienyl, 1,3-cycloheptadienyl, 1,3,5-cycloheptatrienyl and 1,3,5,7-cyclooctatetraenyl.

The term "alkynyl" used either alone or in compound words, such as "optionally substituted alkynyl" denotes groups formed from straight chain, branched, or mono- or poly- or cyclic alkynes, preferably C 2-6 alkynyl.

Examples of alkynyl include ethynyl, 1-propynyl, 1- and 2butynyl, 2-methyl-2-propynyl, 2-pentynyl, 3-pentynyl, 4pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11tridecynyl, 3-tetradecynyl, 7-hexadecynyl, 3-octadecynyl and the like.

The term "alkoxy" used either alone, or in compound words such as "optionally substituted alkoxy" denotes straight chain or branched alkoxy, preferably C1-7 alkoxy. Examples of alkoxy include methoxy, ethoxy, npropyloxy, isopropyloxy and the different butoxy isomers.

The term "aryloxy" used either alone or in compound words such as "optionally substituted aryloxy" denotes aromatic, heteroaromatic, arylalkoxy or heteroaryl alkoxy, preferably C6-13 aryloxy. Examples of aryloxy include phenoxy, benzyloxy, 1-napthyloxy, and 2-napthyloxy.

The term "acyl" used either alone or in compound words such as "optionally substituted acyl" or "heteroarylacyl" denotes carbamoyl, aliphatic acyl group and acyl group containing an aromatic ring, which is referred to as aromatic acyl or a heterocyclic ring which is referred to as heterocyclic acyl. Examples of acyl include carbamoyl; straight chain of branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanyl, tetradecanoyl, pentadecanoyl, hexadecanoyl, heptadecanoyl, octadecanoyl, nonadecanoyl, and icosanoyl; alkoxycarbonyl such as methoxycarbonyl, ethoxycarbonyl, t butoxycarbonyl, t-pentyloxycarbonyl and heptyloxycarbonyl; cycloalkylcarbonyl such as cyclopropylcarbonyl cycle cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutyl, phenylpentanoyl and phenylhexanoyl) and naphthylalkanoyl (e.g. naphthylacetyl, naphthlpropanoyl and naphthylbutanoyl); aralkenoyl such as phenylalkenoyl (e.g. phenylpropenoyl, phenylbutenoyl, phenylmethacrylyl, phenylpentenoyl and phenylhexenoyl and naphthylalkenoy) (e.g. naphthylpropenoyl, napthylbutenoyl and naphthylpentenoyl); aralkoxycarbonyl such as phenylalkoxycarbonyl (e.g. benzyloxycarbonyl); aryloxycarbonyl such as phenoxycarbonyl and naphthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and naphthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienyglyoxyloyl.

The term "aryl" used either alone or in compound words such as "optionally substituted are", "arylalkyl" or"heteroaryl" denotes single, polynuclear, conjugated and fused residues of aromatic hydrocarbons or aromatic heterocyclic ring systems. Examples of aryl include phenyl, biphenyl, terphenyl, quaterphenyl, phenoxyphenyl, naphthyl, tetra anthracenyl, dihydroanthracenyl, benzanthracenyl, dibenzanthracenyl, phenanthrenyl, fluorenyl, pyrenyl, indenyl, azulenyl, chrysenyl, pyridyl, 4-phenylpyridyl, 3-phenylpyridyl, thienyl, furyl, pyrryl, pyrrolyl, furanyl, imadazolyl, pyrrolydinyl, pyridinyl, piperidinyl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. Preferably, the aromatic heterocyclic ring system contains 1 to 4 heteroatoms independently selected from N, O and S and containing up to 9 carbon atoms in the ring.

The term "heterocycle" used either alone or in compound words as "optionally substituted heterocycle" denotes monocyclic or polycyclic heterocyclyl groups containing at least one heteroatom atom selected from nitrogen, sulphur and oxygen. Suitable heterocyclyl groups include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrazinyl, pyridazinyl, triazolyl or tetrazolyl; saturated to 3 to 6-membered heteromonocyclic groups containing 1 to 4 nitrogen atoms, such as, pyrrolidinyl, imidazolidinyl, piperidin or piperazinyl; unsaturated condensed heterocyclic groups containing 1 to 5 nitrogen atoms, such as, indolyl, isoindolyl, benzimidazoyl, quinolyl, isoquinolyl, indazolyl, benzotriazolyl or tetrazolopyridazinyl; unsaturated 3 to 6-membered heteromonocyclic group containing an oxygen atom, such as, pyranyl or furyl; unsaturated 3 to 6-membered heteromonocyclic group containing 1 to 2 sulphur atoms, such as, thienyl; unsaturated 3 to 6-membered heteromonocyclic group containing 1 to 2 oxygen atoms and 1 to 3 nitrogen atoms, such as, oxazolyl, isoxazolyl or oxadiazolyl; saturated 3 to 6-membered heteromonocyclic group containing 1 to 2 oxygen atoms and 1 to 3 nitrogen atoms, such as, morpholinyl; unsaturated condensed heterocyclic group containing 1 to 2 oxygen atoms and 1 to 3 nitrogen atoms, such as, benzoxazolyl or benzoxadiazolyl; unsaturated 3 to 6-membered heteromonocyclic group containing 1 to 2 sulphur atoms and 1 to 3 nitrogen atoms, such as, thiazolyl or thiadiazolyl; saturated 3 to 6-membered heteromonocyclic group containing 1 to 2 sulphur atoms and 1 to 3 nitrogen atoms, such as thiazolidinyl; and unsaturated condensed heterocyclic group containing 1 to 2 sulphur atoms and 1 to 3 nitrogen atoms, such as, benzothiazolyl or benzothiadiazolyl.

In a preferred embodiment, the invention relates to said first method wherein the compounds are synthesized.

In a preferred embodiment, the invention relates to said first method wherein the biological assays are selected from peptide ligand class of GPCRs.

In another aspect the invention provides a compound according to formula 1 in which at least one X is nitrogen, and said X is combined with the corresponding $R_2$-$R_5$ to form a heterocycle. The synthesis of the heterocyclic components of the present invention is disclosed in WO 2004/022572.

In a preferred embodiment, the invention provides a compound according to formula 1 wherein X and $R_2$ combine to form a heterocycle.

In a preferred embodiment, the invention provides a compound according to formula 1 wherein the heterocycle is heteroaryl, including triazoles, benzimidazoles, benzimidazolone, benzimidazolothione, imidazole, hydantoine, thiohydantoine and purine.

DETAILED DESCRIPTION OF THE INVENTION

The embodiments of the invention will be described with reference to the following examples. Where appropriate, the following abbreviations are used.

Ac Acetyl
DTPM 5-Acyl-1,3-dimethylbarbiturate
Ph Phenyl
TBDMS t-Butyldimethylsilyl
TBDPS t-Butyldiphenylsilyl
Bn benzyl
Bz benzoyl
Me methyl
DCE 1,2-dichloroethane
DCM dichloromethane, methylene chloride
Tf trifluoromethanesulfonyl
Ts 4-methylphenylsulfonyl, p-toluenesulfonyl
DMF N,N-dimethylformamide
DMAP N,N-dimethylaminopyridine
α,α-DMT α,α-dimethoxytoluene, benzaldehyde dimethyl acetal
DMSO dimethylsulfoxide
DTT dithiothreitol
DMTST Dimethyl(methylthio)sulphoniumtrifluoro-methanesulphonate
TBAF tetra-n-butylammonium fluoride Part A Preparation of Building Blocks In order to fully enable the invention, there is described below methods for the preparation of certain building blocks used in the preparation of the compounds of the invention. The building blocks described are suitable for both solution and solid phase synthesis of the compounds of the invention.

Example A: Synthesis of a 2,4 Dinitrogen Containing Galactopyranoside Building Block

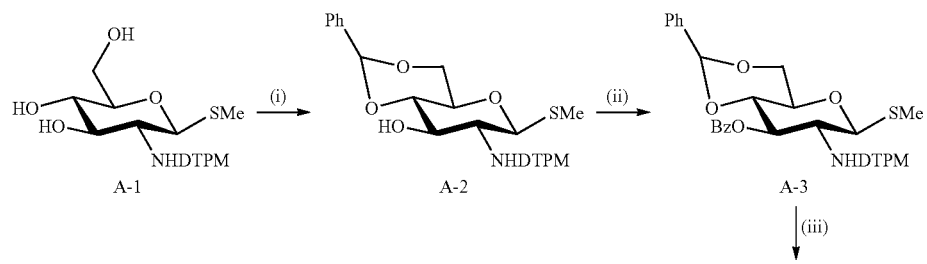

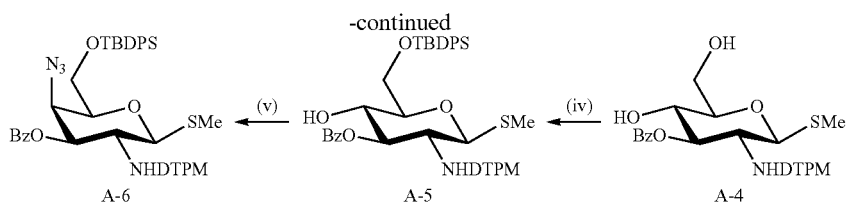

Conditions: (i) α,α-dimethoxytoluene (α,α-DMT), p-toluenesulphonic acid (TsOH), acetonitrile (MeCN), 76° C., 85%;
(ii) Benzoylchloride (BzCl), triethylamine; DCM, 99%; (iii) methanol (MeOH)/MeCN/water, TsOH, 75° C., 98%;
(iv) t-butyldiphenylsilylchloride (TBDPS—Cl), imidazole, pyridine, 120° C., 99%; (v) Tf$_2$O, pyridine, DCM, 0° C., 100%;
(b) NaN$_3$, DMF, 16 hr, RT, 99%.

Example B: Synthesis of a 3-nitrogen Containing Gulopyranoside Building Block

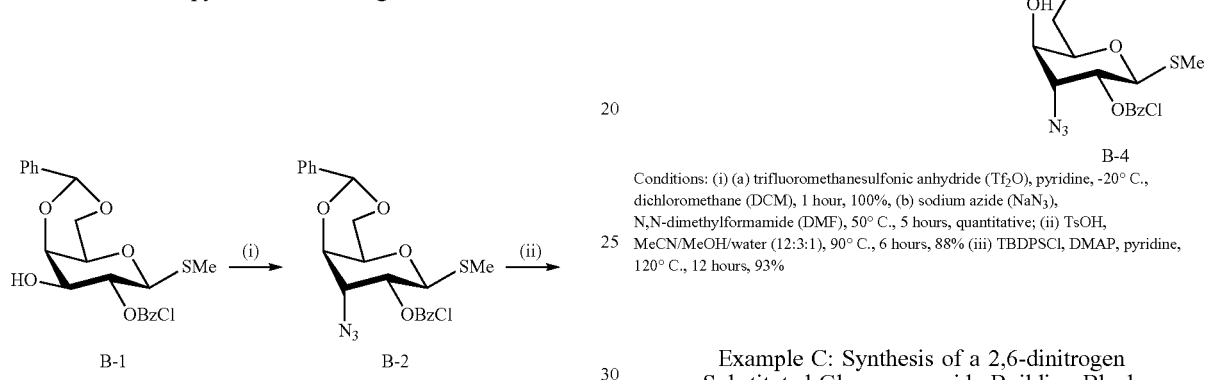

Conditions: (i) (a) trifluoromethanesulfonic anhydride (Tf$_2$O), pyridine, -20° C., dichloromethane (DCM), 1 hour, 100%, (b) sodium azide (NaN$_3$), N,N-dimethylformamide (DMF), 50° C., 5 hours, quantitative; (ii) TsOH, MeCN/MeOH/water (12:3:1), 90° C., 6 hours, 88% (iii) TBDPSCl, DMAP, pyridine, 120° C., 12 hours, 93%

Example C: Synthesis of a 2,6-dinitrogen Substituted Glucopyranoside Building Block

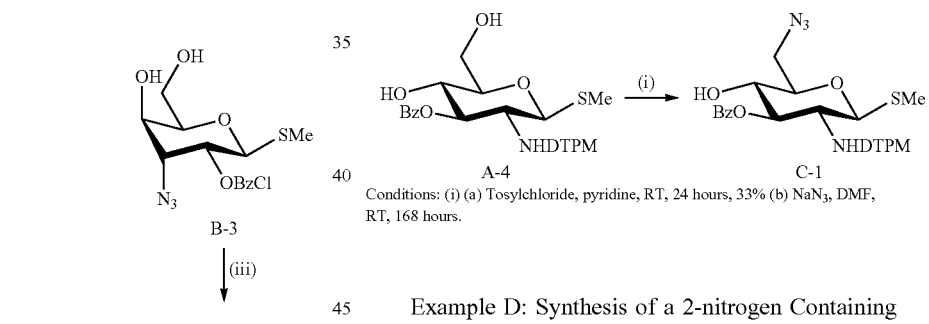

Conditions: (i) (a) Tosylchloride, pyridine, RT, 24 hours, 33% (b) NaN$_3$, DMF, RT, 168 hours.

Example D: Synthesis of a 2-nitrogen Containing Tallopyranoside Building Block

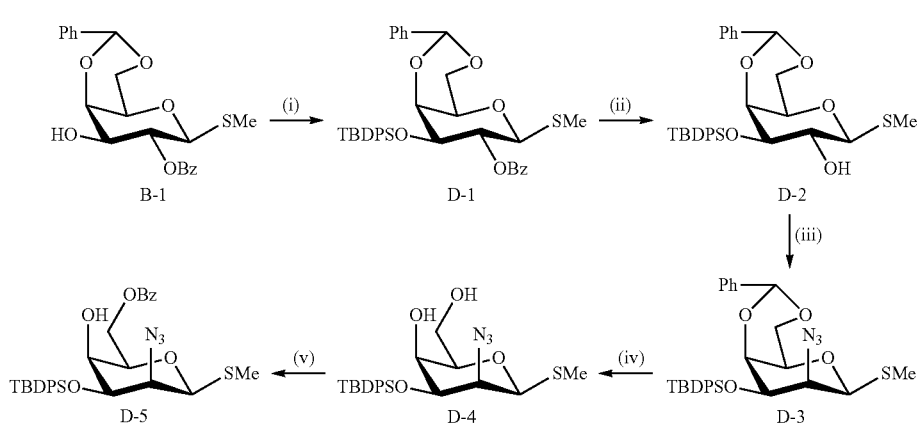

Conditions: (i) TBDPSCl, imidazole, 1,2-DCE, reflux; (ii) NaOMe/MeOH; (iii) (a) Tf$_2$O, pyridine, -20° C., DCM, 1 hour, (b) NaN$_3$, DMF, 50° C., 5 hours; (iv) TsOH, MeCN/MeOH/water; (v) benzoylchloride, DMAP, 1,2-DCE, -20° C.

Example E: Synthesis to 3-nitrogen Containing Altropyranoside Building Block

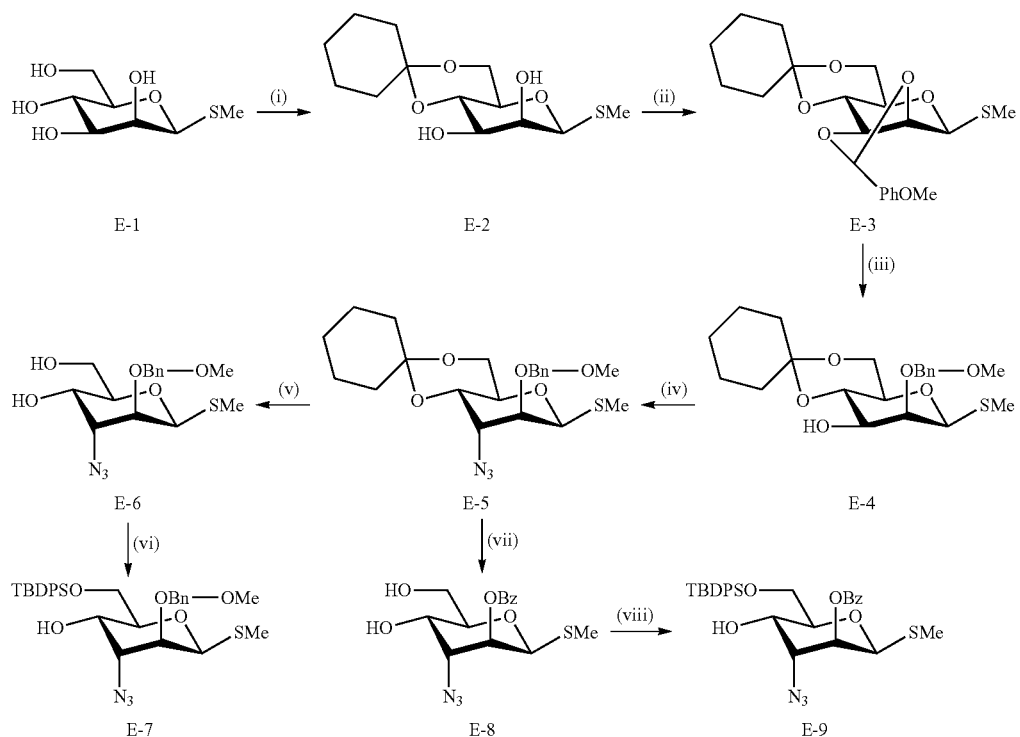

Conditions: (i) cyclohexanone dimethylacetal, TsOH, MeCN; (ii) p-methoxybenzaldehyde dimethylacetal, TsOH, MeCN; (iii) DIBAL, -78° C., diethyl ether; (iv) (a) Tf$_2$O, pyridine, -20° C., DCM, 1 hour, (b) NaN$_3$, DMF, 50° C., 5 hours; (v) TsOH, MeCN/MeOH/water; (vi) TBDPSCl, DMAP, 1,2-DCE; (vii) (a) CAN, (b) BzCl, DMAP, 1,2-DCE, (c) TsOH, MeCN/MeOH/water; (viii) TBDPSCl, DMAP, 1,2-DCE.

Example F: Synthesis 2-nitrogen Containing Glucopyranoside Building Block

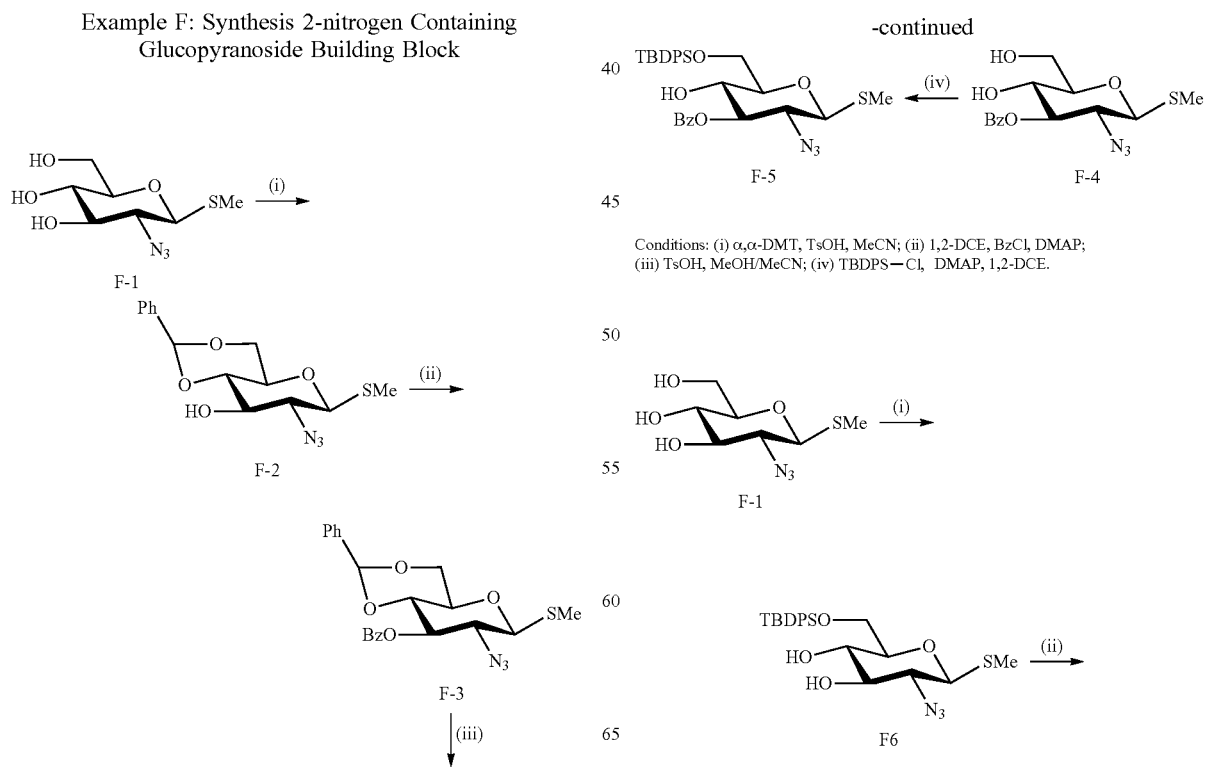

Conditions: (i) α,α-DMT, TsOH, MeCN; (ii) 1,2-DCE, BzCl, DMAP; (iii) TsOH, MeOH/MeCN; (iv) TBDPS—Cl, DMAP, 1,2-DCE.

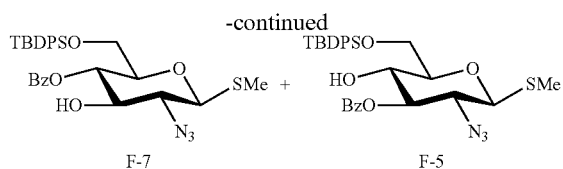

Conditions: (i) TBDPSCl, DMAP, pyridine, 120° C., 0.5 hours, 81%; (ii) a. (Bu)2SnO, MeOH; b. Benzoylchloride, RT, 24 hour;

Example G: Synthesis of a 2-nitrogen Containing Allopyranoside Building Block

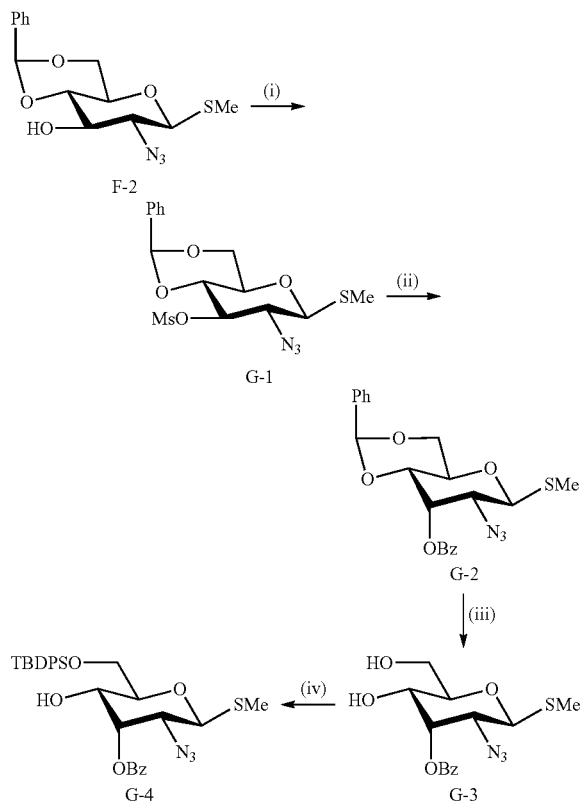

Conditions: (i) DCM/pyridine, MsCl, DMAP, 0° C.; (ii) sodium benzoate, dimethylsulphoxide (DMSO), 140° C.; (iii) TsOH, MeOH/MeCN/water; (iv) TBDPS—Cl, imidazole, DCM, 1 hour, reflux.

The Solid Phase Library Synthesis of Sugars is illustrated in Scheme 1.

The reaction conditions are as follows:

(A) 2P Compound Synthesis: $R_1=R_2=$OMe;
i) 2-naphthalene methanol, DMTST, DCM; TCA-Wang resin, $BF_3.Et_2O$, DCM; iii) NaOMe, methanol; iv a. KOtBu, DMF; b. MeI, DMF; v) HF 'proton sponge', AcOH, DMF, 65° C.; vi) a. KOtBu, DMF; b. MeI, DMF; vii) 1,4-dithio-DL-threitol, KOtBu, DMF; viii) HBTU, Fmoc-β-Ala-OH, DIPEA, DMF; ix) piperidine/DMF (¼); x) TFA, $Et_3SiH$, DCM (B) 3P Compound Synthesis: $R_1=$methyl-2-naphthyl, $R_2=$OMe;
i) 2-naphthalene methanol, DMTST, DCM; ii) TCA-Wang resin, $BF_3.Et_2O$, DCM; iii) NaOMe, methanol; iv) a. KOtBu, DMF; b, 2-bromomethyl-naphthalene, DMF; v) HF 'proton sponge', AcOH, DMF, 65° C.; vi) a. KOtBu, DMF; b. MeI, DMF; vii) 1,4-dithio-DL-threitol, KOtBu, DMF; viii) HBTU, Fmoc-β-Ala-OH, DIPEA, DMF; ix) piperidine/DMF (¼), x) TFA, $Et_3SiH$, DCM (C) 4P Compound Synthesis: $R_1=$methyl-2-naphthyl, $R_2=$4-chlorobenzyl
i) 2-napthalene methanol, DMTST, DCM; ii) TCA-Wang $BF_3.Et_2O$, DCM; iii) NaOMe, methanol; iv) a. KOtBu, DMF; b. 2-bromomethyl-naphthalene, DMF; v) HF 'proton sponge', AcOH, DMF, 65° C.; vi) a. KOtBu, DMF; b. 4-chlorobenzylbromide, DMF; vii) 1,4-dithio-DL-threitol, KOtBu, DMF; viii) HBTU, Fmoc-β-Ala-OH, DIPEA, DMF; ix) piperidine/DMF (¼); x) TFA, $Et_3SiH$, DCM Scheme 1 Solid Phase library Synthesis of sugars

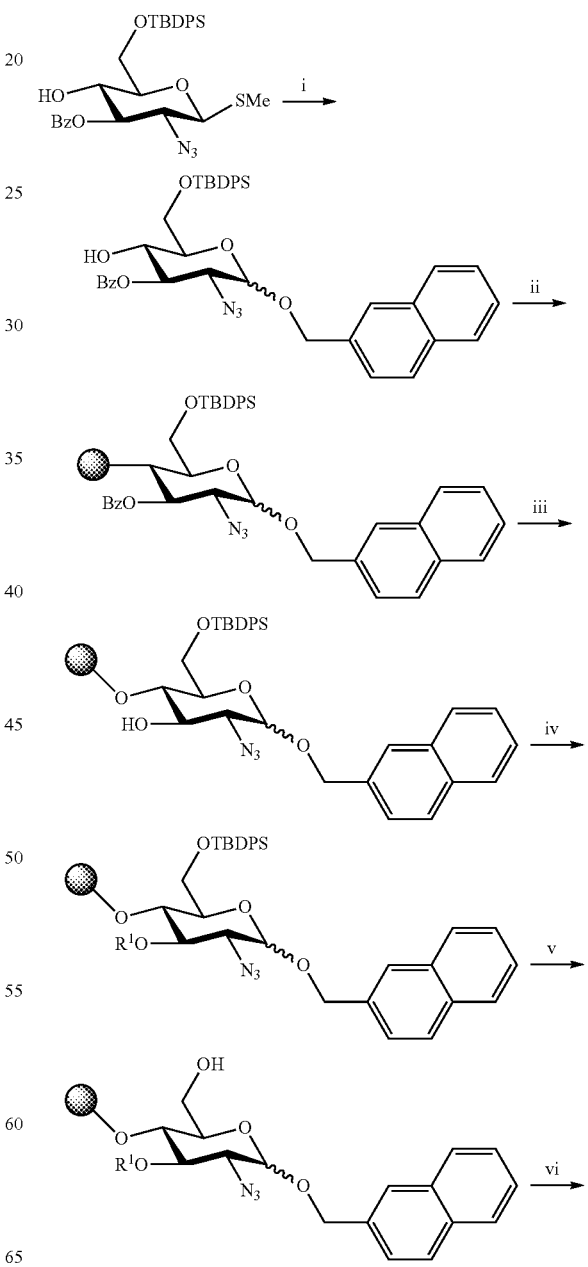

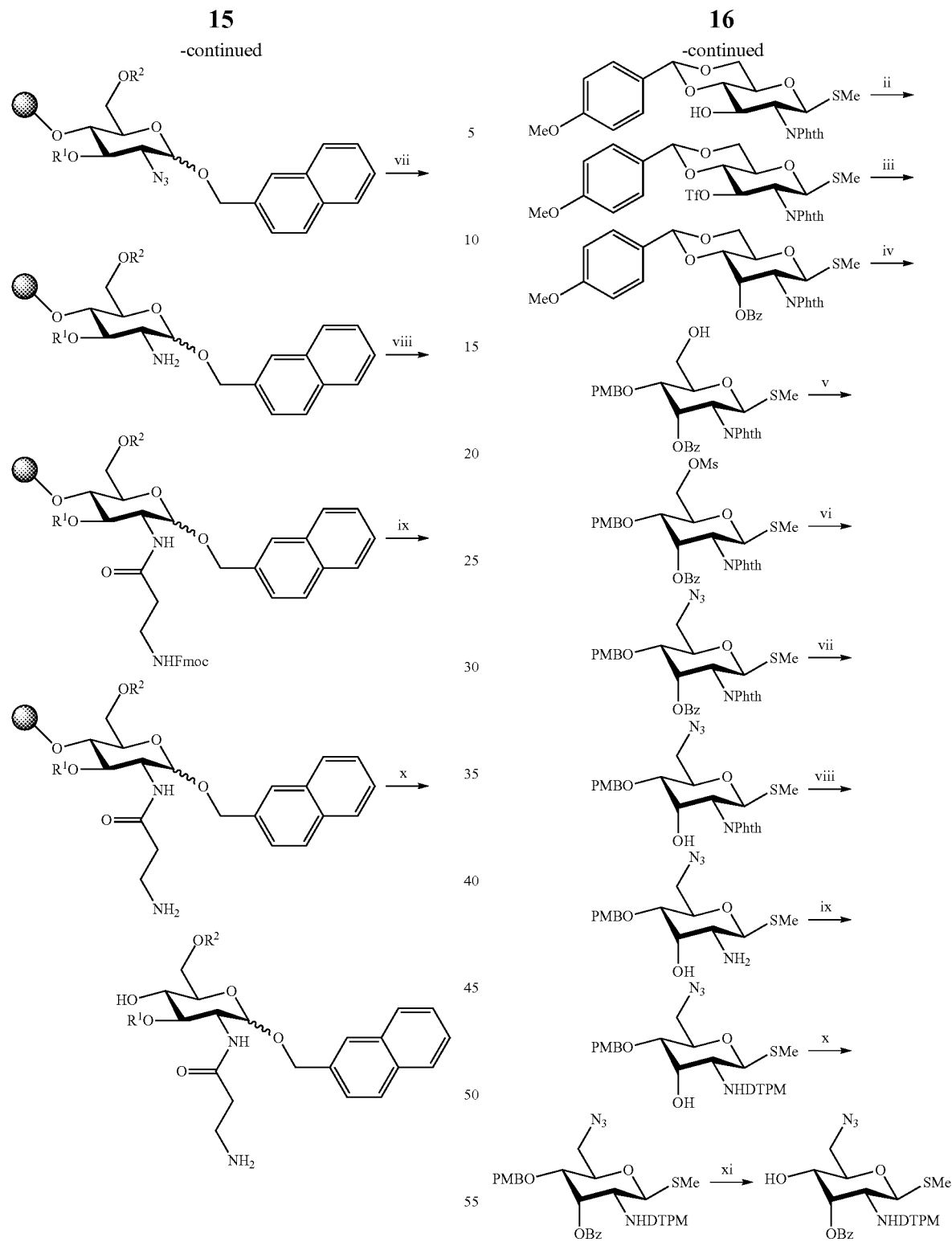

Scheme 2 Synthesis of allose 2,6 building block; an example of synthesis of 2P, 3P and 4P type compound

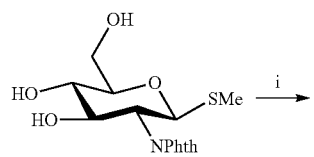

The synthesis of the Allose 2,6N building block is illustrated in Scheme 2. The reaction conditions are as follows:

i) p-methoxybenzaldehyde dimethylacetal, camphorsulfonic acid, N,N-dimethylformamide (DMF); ii) Tf$_2$O, pyridine, dichloromethane (DCM); iii) tetrabutylammonium benzoate, DMF, 55° C.; iv) BH$_3$.THF, Bu$_2$BOTf, DCM; v) methanesulfonylchloride, pyridine, DCM; vi) sodium azide, DMF, 85° C.; vii) sodium methanolate (NaOMe), methanol;

viii) n-butanol, ethylene diamine, reflux; ix) DTPM reagent, methanol; x) benzoic anhydride, pyridine xi) trifluoroacetic acid, triethylsilane, DCM Designing Libraries The design of the libraries is based on the presentation of a positive charge and a crying number of aromatic substituents in different spatial arrangements on a monosaccharide scaffold. Starting with a positive charge and one aromatic displayed on the core scaffold, actives from this first library were elaborated on by further variation and addition of more aromatic substituents to quickly identify highly active molecules.

The first library of compounds comprises two pharmacophoric groups, known as a 2P library, in particular, one containing an aromatic and a positive charge. The library was designed such that each molecule presents two pharmacophoric groups in different relative orientation or presentation (e.g., distance, relative angle, i.e. relative position in, space is different).

Actives from this library were identified and SAR information from this library was used to design subsequent library of compounds wherein each compound may include three pharmacophoric groups, known as a 3P library. Subsequent libraries with four pharmacophoric groups are called 4P library, etc.

Members of significantly improved activity were identified out of the second library and were selected for further drug development.

The method of the invention includes real and virtual libraries.

Thus, the molecules according to formula 1 are well suited for generating iterative scanning libraries, starting from a selected number of pharmacophores (eg, two) in the first library and designing subsequent libraries with additional pharmacophores based on SAR information from the first library, thereby assisting in delineating pharmacophores.

The 2P and 3P library of compounds were synthesized according to the budding blocks as described in Examples A-G.

The 2P library (Table 1) was designed to scan molecular diversity for 3P molecules, comprising an aromatic and a positive charge.

The 2P library was screened for biological activity and the results are given in Table 1.

Similarly, the 3P library was designed to scan molecular diversity for 3P molecules. Design of 3P library resulted from SAR obtained from 2P library in Table 1.

The 3P library was screened for biological activity and the results are given in Table 2.

A visual analysis of the results according to Table 1 (2P library) and Table 2 (3P Library) indicates that:
1. 1, 2 allose substitution according to formula 0.3 (and Scaffold C/D) presents the most active arrangement of molecules in the library wherein Z is oxygen, $R_1$ is naphthyl and $R_2$ is propylamine or ethylamine.

These compounds represent most actives at low mM range, and are suitable candidates for further drug development.

2. $R_1$ as naphthyl is more active than the corresponding p-chlorobenzyl substituent.
3. 1, 2 allose according to formula 3 (Scaffold C/D) is more active than the corresponding 1, 2 glucose conformation (Scaffold A/B).
4. 1. 2 substitution according to formula 3 (Scaffold C/D) is more active then the corresponding 2, 6 substitution according the formula 4 (Scaffold G)

5. $R_2$ as propylamine and ethylamine are more active than methylamine wherein Z, $R_1$ and $R_2$ are as described above.
6. 2, 3 allose substitution according to formula 3 (Scaffold C/D) presents the more actives wherein $R_2$ is ethylamine, and $R_3$ is p-chlorobenzyl compared to corresponding $R_2$ as propylamine and ethylamine wherein R3 is p-chlorobenzyl substituent, and also wherein $R_2$ is methylamine, ethylamine or propylamine and R3 is naphthyl.
7. 2, 3 glucose substitution according to formula 3 (scaffold A/B) presents the more actives wherein $R_2$ propylamine and $R_3$ is naphthyl compared to corresponding $R_2$ as methylamine or ethylamine, and also wherein $R_2$ is methylamine, ethylamine or propylamine and $R_3$ is p-chlorobenzyl.
8. 2, 4 and 3, 4 substitutions according to formula 3 (Scaffold G) present the least actives.

Part B

Biological Assays

Example H: In Vitro Screening of Compounds Against Somatostatin Subtypes SSTR-1 to SSTR-5

General Method

Receptor membrane preparations containing the desired cloned receptor (for example cloned human somatostatin receptor subtype 5, SSTR5) and radiolabeled ligand were diluted at the concentration required for testing and according to the specific parameters associated with the selected receptor-ligand combination, including receptor $B_{max}$, ligand $K_d$ and any other parameters necessary to optimize the experimental conditions. When tested for competition activity to the reference ligand, "compound" was mixed with membrane suspension and the radiolabeled reference ligand (with or without an excess of unlabeled ligand to the receptor for determination of non-specific binding) and incubated at the temperature required by internal standard operating procedures. Following incubation, the binding reaction was stopped by the addition of ice-cold washing buffer and filtered on appropriate filters, which are then counted. Data analysis and curve-fitting was performed with XLfit (IDBS).

Preparation of Compounds 10 mM solutions of test compounds in 100% DMSO were prepared, ~160 µl was used for each dilution (20 µl/well in triplicate).

A 1.25 mM assay stock was prepared by making a 1:8 dilution of the 10 mM solution. To 30 µL of the 10 mM solution was added 210 µL milli-Q $H_2O$. A 1:5 dilution series in milli-Q $H_2O$ was then prepared.

|  |  | Final concentration in SST4 assay | Final concentration in SST5 assay |
|---|---|---|---|
| A. | 240 µL of 1.25 mM | 0.25 mM | 0.125 mM |
| B. | 48 µL A + 192 µL mQ | 0.05 mM | 0.025 mM |
| C. | 24 µL B + 192 µL mQ | 0.01 mM | 0.005 mM |
| etc |  |  |  |

Assays were performed in triplicate at each concentration within the 1:5 dilution series: 250 µM, 50 µM, 10 µM, 2 mM, 0.4 µM, 0.08 µM, 0.016 µM, 0.0032 µM, etc. (for SST4 assay and 125 µM, 10 µM, 2 µM, 1 µM, 0.5 µM, etc (for SST5 assay).

Fitter Plate Assay for SST5 Receptor

Human SST5 somatostatin receptor was transfected into HEK-293 EBNA cells. Membranes were suspended in assay buffer (50 mM Tris-HCl, 1 mM EGTA, 5 mM $MgCl_2$, 10% sucrose, pH 7.5). The receptor concentration ($B_{max}$) was 0.57 pmol/mg protein $K_d$ for [$^{125}$I]SST-14 Binding 0.31 nM, volume 0.4 ml per vial (400 microassays/vial), and protein concentration 1.03 mg/ml.

After thawing the frozen receptor preparation rapidly, receptors were diluted with binding buffer, homogenized, and kept on ice.

1. Use Multiscreen glass fiber filter plates (Millipore, Cat No MAFCNOB10) precoated with 0.5% PEI for ~2 hr at 4° C. Before use add 200 µl/well assay buffer and filter using Multiscreen Separation System.
2. Incubate 5.5 µg of membranes (40 µl of a 1:40 dilution), buffer and [$^{125}$I]SST-14 (4 nM, ~80 000 cpm, 2000 Ci/mmol) in a total volume of 200 µl for 60 min at 25° C. Calculate IC50 for SST-14 (a truncated version of the natural ligand SST-28) (Auspep, Cat No 2076) and SST-28 (Auspep, Cat No 1638). Prepare serial dilutions (1:5) of compounds, as described above and instead of adding SST-14 in well, add 20 µl of compounds (Table 3).
3. Filter using Multiscreen Separation System with 5×0.2 ml ice-cold Assay buffer.
4. Remove the plastic underdrain and dry plate in oven for 1 hr at 40° C.
5. Seal tape to the bottom of the plate.
6. Add 50 µl/well scintillant (Supermix, Wallac, Cat No 1200-439).
7. Seal and count in the BJET, program 2.

TABLE 3

| Volume (ul) | TB | NSB | Compounds testing |
|---|---|---|---|
| Membranes (5.5 µg/well) | 40 | 40 | 40 |
| Radio-labeled label (~80 000 cpm, ~4 nM) | 40 | 40 | 40 |
| Unlabeled ligand | — | 20 | — |
| $mQH_2O$ | 20 | — | — |
| Compounds | — | — | 20 |
| Assay buffer | 100 | 100 | 100 |
| Total volume (µl) | 200 | 200 | 200 |

TB: total binding
NSB: non-specific binding

Part C

General Experimental Methods

Example I: HPLC Method for Compounds in Tables 1 and 2

The HPLC separation of compounds in Tables 1 and 2 was conducted under Method A or Method B as shown below.
Method A
Column: Agent SB Zorbax C18 4.6×50 mm (5 µm, 80 Å)
LC mobile phase:
5% aqueous MeCN/1 min
100% MeCN/7-12 min
Method B
Column: Agilent SB Zorbax C18 4.6×50 mm (5 µm, 80 Å)
LC mobile phase:
5% aq MeCN/1 min
30% aq MeCN/3 min
40% aq MeCN/12 min
100% MeCN/13-15 min
Key to Building Blocks for Tables 1 and 2
Table 1: *% SST5 radio-ligand binding displaced at conc (µM) for 2P library of compounds
Table 2: *% SST5 radio-ligand binding displaced at conc (µM) for 3P library of compounds; $R_4$=X30; compounds 60-63, 119 and 156-159 are comparative compounds from 2P library
"++": % SST5 radio-ligand binding displaced at conc (µM) >60%
"+": % SST5 radio-ligand binding displaced at conc (µM) 60>+>40%
"−": % SST5 radio-ligand binding displaced at conc (µM) −<40%
Blank: not determined
RT: retention time/minutes
M+H: mass ion+1

TABLE 1

Biological activity of example 2P library

| Object ID | Scaffold | R1 | R2 | R3 | R4 | R5 | conc 500 | conc 250 | conc 50* | RT | M + H |
|---|---|---|---|---|---|---|---|---|---|---|---|
| 1 | E | — | X15 | X2 | X30 | X24 | | | | 3.24 | 449.58 |
| 2 | A | X7 | X20 | X24 | X30 | X24 | | | | 3.4 | 383.46 |
| 3 | A | X7 | X15 | X24 | X30 | X24 | | | | 3.42 | 397.48 |
| 4 | E | — | X20 | X2 | X30 | X24 | | | | 3.49 | 435.55 |
| 5 | A | X2 | X20 | X24 | X30 | X24 | ++ | + | − | 3.88 | 419.21 |
| 6 | A | X2 | X15 | X24 | X30 | X24 | ++ | + | − | 3.83 | 433.23 |
| 7 | E | — | X19 | X24 | X30 | X3 | − | − | − | 3.42 | 405.12 |
| 8 | E | — | X19 | X24 | X30 | X2 | ++ | + | − | 3.81 | 421.17 |
| 9 | E | — | X19 | X3 | X30 | X24 | − | − | − | 3.62 | 405.12 |
| 10 | E | — | X19 | X2 | X30 | X24 | − | − | − | 4.03 | 421.17 |
| 11 | A | X3 | X19 | X24 | X30 | X24 | − | − | − | 3.39 | 389.14 |
| 12 | A | X2 | X19 | X24 | X30 | X24 | − | − | − | 4.08 | 405.19 |
| 13 | B | X3 | X19 | X24 | X30 | X24 | − | − | − | 3.4 | 389.14 |
| 14 | B | X2 | X19 | X24 | X30 | X24 | − | − | − | 3.88 | 405.19 |
| 15 | E | — | X20 | X24 | X30 | X3 | − | − | − | 3.25 | 419.13 |
| 16 | E | — | X20 | X24 | X30 | X2 | + | − | − | 3.59 | 435.19 |
| 17 | E | — | X20 | X3 | X30 | X24 | − | − | − | 3.68 | 419.13 |

TABLE 1-continued

Biological activity of example 2P library

| Object ID | Scaffold | R1 | R2 | R3 | R4 | R5 | conc 500 | conc 250 | conc 50* | RT | M + H |
|---|---|---|---|---|---|---|---|---|---|---|---|
| 18 | E | — | X20 | X2 | X30 | X24 | − | − | − | 4.06 | 435.19 |
| 19 | A | X3 | X20 | X24 | X30 | X24 | ++ | − | − | 3.56 | 403.16 |
| 20 | B | X3 | X20 | X24 | X30 | X24 | + | − | − | 3.37 | 403.16 |
| 21 | B | X2 | X20 | X24 | X30 | X24 | ++ | + | − | 3.7 | 419.21 |
| 22 | E | — | X15 | X24 | X30 | X3 | − | − | − | 3.22 | 433.15 |
| 23 | E | — | X15 | X24 | X30 | X2 | + | − | − | 3.59 | 449.2 |
| 24 | E | — | X15 | X3 | X30 | X24 | − | − | − | 3.7 | 433.15 |
| 25 | E | — | X15 | X2 | X30 | X24 | + | − | − | 4.06 | 449.2 |
| 26 | E | X3 | X15 | X24 | X30 | X24 | ++ | − | − | 3.57 | 417.17 |
| 27 | B | X3 | X15 | X24 | X30 | X24 | − | − | − | 3.4 | 417.17 |
| 28 | B | X2 | X15 | X24 | X30 | X24 | ++ | − | − | 3.68 | 433.23 |
| 29 | F | — | X19 | X24 | X30 | X3 | − | − | − | 3.55 | 405.12 |
| 30 | F | — | X19 | X24 | X30 | X2 | + | − | − | 3.84 | 421.17 |
| 31 | F | — | X19 | X3 | X30 | X24 | + | − | − | 3.75 | 405.12 |
| 32 | F | — | X19 | X2 | X30 | X24 | − | − | − | 4.05 | 421.17 |
| 33 | C | X3 | X19 | X24 | X30 | X24 | − | − | − | 3.38 | 389.14 |
| 34 | C | X2 | X19 | X24 | X30 | X24 | − | − | − | 3.72 | 405.19 |
| 35 | D | X3 | X19 | X24 | X30 | X24 | − | − | − | 3.41 | 389.14 |
| 36 | D | X2 | X19 | X24 | X30 | X24 | + | − | − | 3.77 | 405.19 |
| 37 | F | — | X20 | X3 | X30 | X24 | − | − | − | 3.76 | 419.13 |
| 38 | C | X3 | X20 | X24 | X30 | X24 | ++ | + | − | 3.33 | 403.16 |
| 39 | D | X3 | X20 | X24 | X30 | X24 | ++ | − | − | 3.44 | 403.16 |
| 40 | D | X2 | X20 | X24 | X30 | X24 | ++ | ++ | − | 3.8 | 419.21 |
| 41 | F | — | X15 | X24 | X30 | X3 | − | − | − | 3.51 | 433.15 |
| 42 | F | — | X15 | X24 | X30 | X2 | + | − | − | 3.81 | 449.2 |
| 43 | F | — | X15 | X3 | X30 | X24 | − | − | − | 3.66 | 433.15 |
| 44 | D | X3 | X15 | X24 | X30 | X24 | ++ | − | − | 3.51 | 417.17 |
| 45 | D | X2 | X15 | X24 | X30 | X24 | ++ | + | − | 3.86 | 433.23 |
| 46 | G | — | X24 | X3 | X19 | X30 | − | − | − | 3.31 | 386.14 |
| 47 | G | — | X19 | X2 | X24 | X30 | − | − | − | 3.27 | 402.2 |
| 48 | G | — | X19 | X24 | X8 | X30 | − | − | − | 2.48 | 352.18 |
| 49 | G | — | X2 | X24 | X19 | X30 | − | − | − | 3.64 | 388.18 |
| 50 | G | — | X8 | X24 | X19 | X30 | − | − | − | 2.61 | 352.18 |
| 51 | G | — | X24 | X3 | X20 | X30 | − | − | − | 3.08 | 400.16 |
| 52 | G | — | X2 | X24 | X20 | X30 | − | − | − | 3.46 | 402.2 |
| 53 | G | — | X8 | X24 | X20 | X30 | − | − | − | 2.73 | 366.2 |
| 54 | G | — | X24 | X3 | X15 | X30 | − | − | − | 3.27 | 414.17 |
| 55 | G | — | X2 | X24 | X15 | X30 | − | − | − | 3.79 | 416.21 |
| 56 | G | — | X8 | X24 | X15 | X30 | − | − | − | 2.78 | 380.21 |
| 57 | F | — | X20 | X2 | X30 | X24 | − | − | − | 4.01 | 435.19 |
| 58 | F | — | X15 | X2 | X30 | X24 | − | − | − | 4.08 | 449.2 |
| 59 | C | X2 | X20 | X24 | X30 | X24 | ++ | ++ | + | 3.74 | 419.21 |

TABLE 2

Biological activity of example 3P library

| Object ID | Scaffold | R1 | R2 | R3 | R5 | conc 500 | conc 250 | conc 50 | conc 10 | conc 1.0 | conc 0.5 | conc 0.25 | conc 0.10 | conc 0.001* | RT | M + H |
|---|---|---|---|---|---|---|---|---|---|---|---|---|---|---|---|---|
| 60 | A | X2 | X20 | X24 | X24 | ++ | + | − | | | | | | | 3.88 | 419.21 |
| 61 | B | X2 | X20 | X24 | X24 | ++ | + | − | | | | | | | 3.7 | 419.21 |
| 62 | D | X2 | X20 | X24 | X24 | ++ | ++ | − | | | | | | | 3.8 | 419.21 |
| 63 | C | X2 | X20 | X24 | X24 | ++ | ++ | + | | | | | | | 3.72 | 419.21 |
| 64 | C and D | X2 | X20 | X8 | X24 | | | | ++ | ++ | ++ | + | − | | 4.98 | |
| 65 | C and D | X2 | X20 | X8 | X24 | | | | ++ | | | | | | 4.98 | |
| 66 | C and D | X2 | X20 | X3 | X24 | | | | ++ | ++ | ++ | − | − | | 5.25 | |
| 67 | C and D | X2 | X20 | X3 | X24 | | | | ++ | | | | | | 5.25 | |
| 68 | C and D | X2 | X20 | X1 | X24 | | | | ++ | ++ | ++ | − | − | − | 5.49 | |
| 69 | C and D | X2 | X20 | X2 | X24 | | | | ++ | ++ | ++ | ++ | + | | 5.23 | |
| 70 | C and D | X2 | X20 | X3 | X2 | | | | | + | − | | | | 5.85 | |
| 71 | C and D | X2 | X20 | X3 | X8 | | | | | ++ | − | | | | 5.61 | |
| 72 | C and D | X2 | X20 | X3 | X3 | | | | | ++ | | | | | 5.51 | |
| 73 | C and D | X2 | X20 | X2 | X2 | | | | | + | − | | | | 5.95 | |
| 74 | C and D | X2 | X20 | X2 | X8 | | | | | ++ | − | | | | 5.45 | |
| 75 | C and D | X2 | X20 | X2 | X3 | | | | | ++ | − | | | | 6.46 | |
| 76 | C and D | X2 | X20 | X8 | X2 | | | | | ++ | − | | | | 5.7 | |
| 77 | C and D | X2 | X20 | X8 | X8 | | | | | ++ | − | | | | 5.01 | |
| 78 | C and D | X2 | X20 | X8 | X3 | | | | | ++ | + | | | | 5.37 | |
| 79 | B | X2 | X20 | X2 | X2 | | | | | ++ | − | | | | 10.31 | |
| 80 | A | X2 | X20 | X2 | X2 | | | | | ++ | − | | | | 10.88 | |
| 81 | B | X2 | X20 | X2 | X8 | | | | | ++ | − | | | | 8.02 | |

TABLE 2-continued

Biological activity of example 3P library

| Object ID | Scaffold | R1 | R2 | R3 | R5 | conc 500 | conc 250 | conc 50 | conc 10 | conc 1.0 | conc 0.5 | conc 0.25 | conc 0.10 | conc 0.001* | RT | M + H |
|---|---|---|---|---|---|---|---|---|---|---|---|---|---|---|---|---|
| 82 | A | X2 | X20 | X2 | X8 | | | | | ++ | + | | | | 8.68 | |
| 83 | B | X2 | X20 | X2 | X3 | | | | | ++ | − | | | | 9.39 | |
| 84 | A | X2 | X20 | X2 | X3 | | | | | ++ | − | | | | 10.24 | |
| 85 | D | X2 | X20 | X2 | X24 | | | | ++ | | ++ | | | | 50.92 | |
| 86 | C | X2 | X20 | X2 | X24 | | | | ++ | | ++ | | | | 54.37 | |
| 87 | A or B | X2 | X20 | X8 | X24 | | | | | − | − | | | | 3.78 | 495.59 |
| 88 | A or B | X2 | X20 | X8 | X24 | | | | | − | − | | | | 3.86 | 495.59 |
| 89 | A or B | X2 | X20 | X3 | X24 | | | | | − | − | | | | 3.95 | 530.03 |
| 90 | A or B | X2 | X20 | X3 | X24 | | | | | ++ | + | | | | 3.97 | 530.03 |
| 91 | A or B | X2 | X20 | X1 | X24 | | | | | − | − | | | | 4.5 | 571.69 |
| 92 | A or B | X2 | X20 | X2 | X24 | | | | | + | − | | | | 4.33 | 545.65 |
| 93 | A and B | X2 | X20 | X24 | X8 | | | | | + | − | | | | 4.13 | 495.59 |
| 94 | A or B | X2 | X20 | X24 | X3 | | | | | − | − | | | | 4.33 | 530.03 |
| 95 | A or B | X2 | X20 | X24 | X3 | | | | | − | − | | | | 4.33 | 530.03 |
| 96 | A or B | X2 | X20 | X24 | X1 | | | | | − | − | | | | 4.77 | 571.69 |
| 97 | A and B | X2 | X20 | X24 | X2 | | | | | + | − | | | | 4.52 | 545.65 |
| 98 | A | X2 | X20 | X2 | X24 | | | | | ++ | + | | | | 5.45 | 545.65 |
| 99 | A | X2 | X31 | X2 | X24 | | | | | + | − | | | | 5.07 | 559.67 |
| 100 | A | X2 | X32 | X2 | X24 | | | | | ++ | + | | | | 5.05 | 559.67 |
| 101 | A | X2 | X33 | X2 | X24 | | | | | + | − | | | | 4.79 | 557.66 |
| 102 | A | X2 | X34 | X2 | X24 | | | | | − | − | | | | 6.24 | 613.77 |
| 103 | A | X2 | X35 | X2 | X24 | | | | | ++ | + | | | | 5.85 | 585.71 |
| 104 | A | X2 | X36 | X2 | X24 | | | | | − | − | | | | 6.33 | 599.74 |
| 105 | A | X2 | X37 | X2 | X24 | | | | | − | − | | | | 6.72 | 599.74 |
| 106 | A | X2 | X45 | X2 | X24 | | | | | − | − | | | | 4.96 | 573.7 |
| 107 | A | X2 | X20 | X46 | X24 | | | | | ++ | ++ | | | | 4.22 | 530.03 |
| 108 | A | X2 | X20 | X47 | X24 | | | | | ++ | + | | | | 4.87 | 564.48 |
| 109 | A | X2 | X20 | X48 | X24 | | | | | ++ | − | | | | 4.98 | 530.03 |
| 110 | A | X2 | X20 | X49 | X24 | | | | | ++ | ++ | | | | 4.43 | 546.64 |
| 111 | A | X2 | X20 | X50 | X24 | | | | | − | − | | | | 5.44 | 552.66 |
| 112 | A | X2 | X20 | X51 | X24 | | | | | ++ | + | | | | 3.78 | 546.64 |
| 113 | A | X2 | X20 | X52 | X24 | | | | | ++ | ++ | | | | 5.71 | 564.48 |
| 114 | A | X2 | X20 | X9 | X24 | | | | | ++ | ++ | | | | 5.89 | 545.65 |
| 115 | A | X2 | X20 | X53 | X24 | | | | | ++ | + | | | | 5.8 | 564.48 |
| 116 | A | X2 | X20 | X54 | X24 | | | | | ++ | + | | | | 4.43 | 546.64 |
| 117 | A | X2 | X20 | X55 | X24 | | | | | ++ | ++ | | | | 5.71 | 564.48 |
| 118 | A | X2 | X20 | X56 | X24 | | | | | ++ | ++ | | | | 6.9 | 587.68 |
| 119 | A | X2 | X15 | X24 | X24 | ++ | + | − | | | | | | | | |
| 120 | A and B | X2 | X15 | X8 | X24 | | | | ++ | | + | | | | 4.29/4.57 | |
| 121 | A and B | X2 | X15 | X24 | X1 | | | | + | | + | | | | 5.4 | |
| 122 | A and B | X2 | X15 | X24 | X2 | | | | ++ | | ++ | | | | 5.18 | |
| 123 | A and B | X2 | X15 | X24 | X8 | | | | − | | − | | | | 4.78 | |
| 124 | A and B | X2 | X15 | X24 | X3 | | | | + | | − | | | | 5.07 | |
| 125 | A and B | X2 | X15 | X24 | X4 | | | | + | | − | | | | 4.28 | |
| 126 | C and D | X2 | X15 | X8 | X24 | | | | ++ | + | + | − | − | | 4.97 | |
| 127 | C and D | X2 | X15 | X3 | X24 | | | | ++ | ++ | ++ | − | − | | 5.17 | |
| 128 | C and D | X2 | X15 | X1 | X24 | | | | ++ | + | ++ | − | − | | 5.45 | 585.71 |
| 129 | C and D | X2 | X15 | X2 | X24 | | | | ++ | ++ | − | + | − | | 5.18 | 559.67 |
| 130 | A and B | X2 | X15 | X4 | X24 | | | | ++ | | | | | | | |
| 131 | A and B | X2 | X15 | X1 | X24 | | | | ++ | | | | | | | |
| 132 | A and B | X2 | X15 | X2 | X24 | | | | ++ | | | | | | | |
| 133 | A and B | X2 | X15 | X3 | X24 | | | | ++ | | | | | | | |
| 134 | A | X2 | X15 | X3 | X24 | | | | ++ | ++ | ++ | ++ | + | | 4.78 | |
| 135 | A | X2 | X15 | X3 | X2 | | | | | ++ | − | | | | 9.87 | |
| 136 | A | X2 | X15 | X3 | X8 | | | | | ++ | − | | | | 7.82 | |
| 137 | A | X2 | X15 | X3 | X3 | | | | | ++ | − | | | | 9.32 | |
| 138 | A | X2 | X38 | X2 | X24 | | | | | − | − | | | | 3.67 | 574.69 |
| 139 | A | X2 | X39 | X2 | X24 | | | | | + | − | | | | 5.07 | 573.7 |
| 140 | A | X2 | X40 | X2 | X24 | | | | | ++ | ++ | | | | 4.96 | 573.7 |
| 141 | A | X2 | X41 | X2 | X24 | | | | | − | − | | | | 5.16 | 587.73 |
| 142 | A | X2 | X53 | X2 | X24 | | | | | ++ | + | | | | 5.69/7.43 | 599.74 |
| 143 | A | X2 | X42 | X2 | X24 | | | | | − | − | | | | 5.98 | 613.77 |
| 144 | A | X2 | X15 | X46 | X24 | | | | | ++ | + | | | | 4.34 | 544.06 |
| 145 | A | X2 | X15 | X47 | X24 | | | | | ++ | + | | | | 5.07 | 578.5 |
| 146 | A | X2 | X15 | X48 | X24 | | | | | ++ | + | | | | 5.05 | 544.06 |
| 147 | A | X2 | X15 | X49 | X24 | | | | | ++ | + | | | | 4.5 | 560.66 |
| 148 | A | X2 | X15 | X50 | X24 | | | | | − | − | | | | 5.34 | 566.69 |
| 149 | A | X2 | X15 | X51 | X24 | | | | | + | − | | | | 3.95 | 560.86 |
| 150 | A | X2 | X15 | X52 | X24 | | | | | ++ | ++ | | | | 5.78 | 578.5 |
| 151 | A | X2 | X15 | X9 | X24 | | | | | ++ | + | | | | 5.78 | 559.67 |
| 152 | A | X2 | X15 | X53 | X24 | | | | | ++ | + | | | | 5.97 | 578.5 |
| 153 | A | X2 | X15 | X54 | X24 | | | | | ++ | ++ | | | | 4.32 | 580.66 |
| 154 | A | X2 | X15 | X55 | X24 | | | | | ++ | ++ | | | | 5.88 | 578.5 |
| 155 | A | X2 | X15 | X56 | X24 | | | | | ++ | ++ | | | | 7.25 | 601.71 |
| 156 | A | X3 | X19 | X24 | X24 | − | − | − | | | | | | | 3.39 | 389.14 |

TABLE 2-continued

Biological activity of example 3P library

| Object ID | Scaffold | R1 | R2 | R3 | R5 | conc 500 | conc 250 | conc 50 | conc 10 | conc 1.0 | conc 0.5 | conc 0.25 | conc 0.10 | conc 0.001* | RT | M + H |
|---|---|---|---|---|---|---|---|---|---|---|---|---|---|---|---|---|
| 157 | B | X3 | X19 | X24 | X24 | − | − | − | | | | | | | | |
| 158 | C | X3 | X19 | X24 | X24 | − | − | − | | | | | | | 3.38 | 389.14 |
| 159 | D | X3 | X19 | X24 | X24 | − | − | − | | | | | | | | |
| 160 | C and D | X3 | X19 | X8 | X24 | | | | − | − | − | | − | − | 4.8 | |
| 161 | C and D | X3 | X19 | X3 | X24 | | | | ++ | − | − | | − | − | 5.14 | |
| 162 | C and D | X3 | X19 | X1 | X24 | | | | + | − | − | − | − | − | 5.45 | 542.04 |
| 163 | C and D | X3 | X19 | X2 | X24 | | | | ++ | − | − | − | − | − | 5.2 | |
| 164 | C and D | X3 | X43 | X24 | X2 | | | | + | − | | | | | 3.45 | |
| 165 | C and D | X3 | X44 | X24 | X2 | | | | ++ | − | | | | | 4 | |
| 166 | A and B | X3 | X43 | X24 | X2 | | | | ++ | − | | | | | 3.59 | |
| 167 | A and B | X3 | X44 | X24 | X2 | | | | ++ | ++ | | | | | 3.97 | |
| 168 | A or B | X3 | X19 | X8 | X24 | | | | | − | − | − | | | | |
| 169 | A or B | X3 | X19 | X8 | X24 | | | | | − | − | | | | | |
| 170 | A or B | X3 | X19 | X3 | X24 | | | | | − | − | | | | | |
| 171 | A or B | X3 | X19 | X3 | X24 | | | | | − | − | | | | | |
| 172 | A or B | X3 | X19 | X1 | X24 | | | | | − | − | | | | | |
| 173 | A or B | X3 | X19 | X1 | X24 | | | | | − | − | | | | | |
| 174 | A or B | X3 | X19 | X2 | X24 | | | | | − | − | | | | | |
| 175 | A or B | X3 | X19 | X2 | X24 | | | | | − | − | | | | | |
| 176 | A and B | X3 | X19 | X24 | X8 | | | | | − | − | | | | 4.88/5.61 | 465.95 |
| 177 | A and B | X3 | X19 | X24 | X3 | | | | | − | − | | | | 6.06/6.52 | 500.39 |
| 178 | A and B | X3 | X19 | X24 | X1 | | | | | − | − | | | | 9.09 | 542.04 |
| 179 | A and B | X3 | X19 | X24 | X2 | | | | | − | − | | | | 7.43 | 516.01 |

Figure 1: Sidearms for Tables 1 and 2

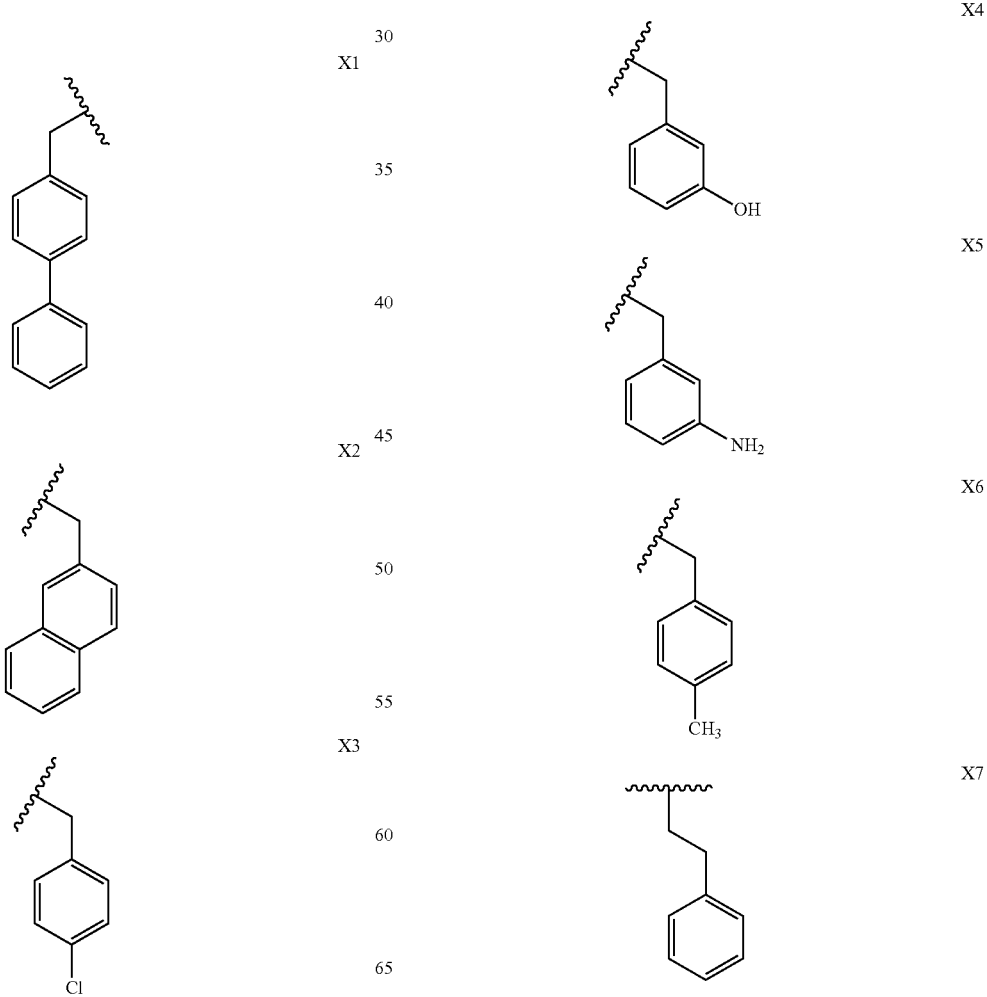

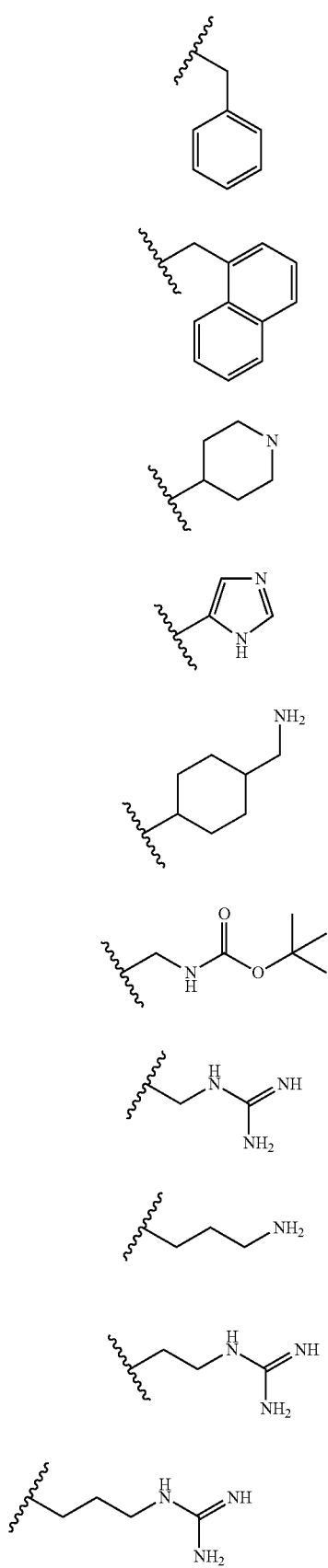
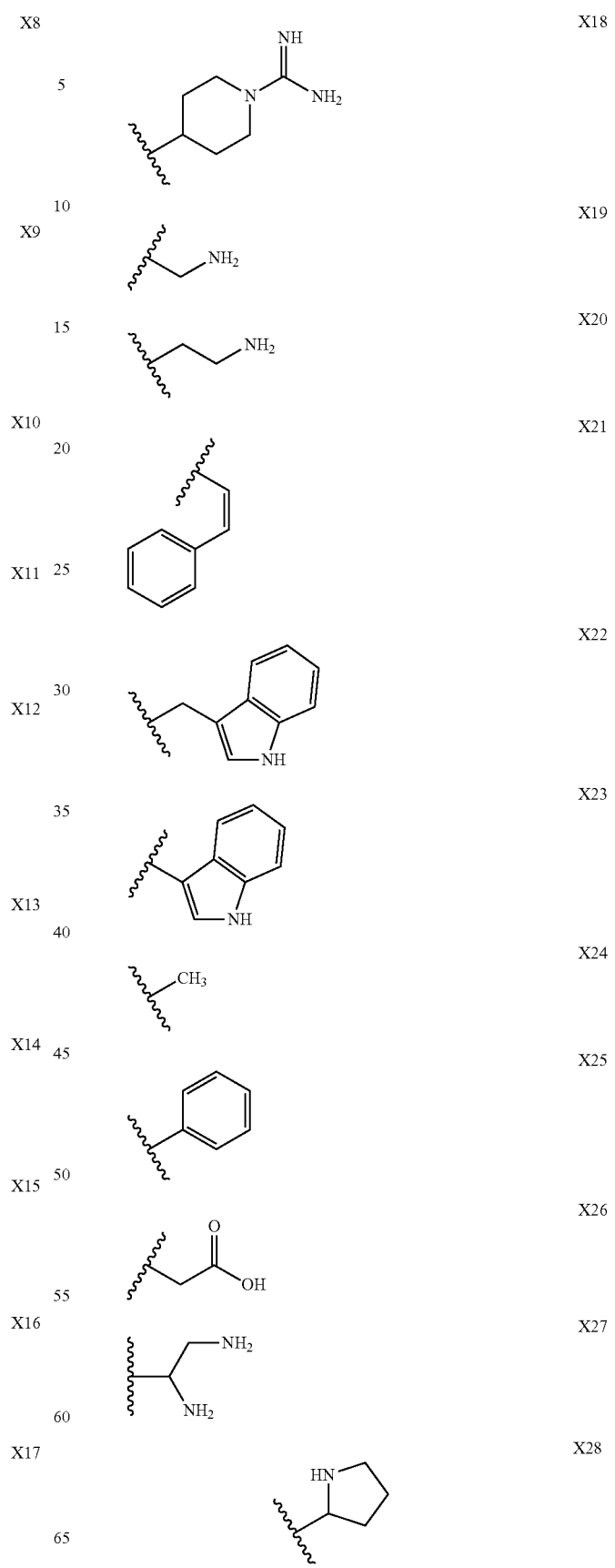

-continued
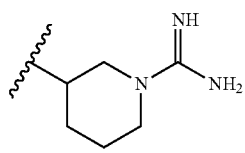 X29
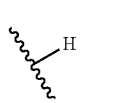 X30
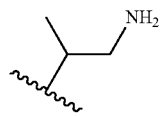 X31
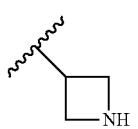 X33
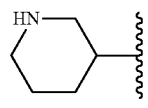 X35
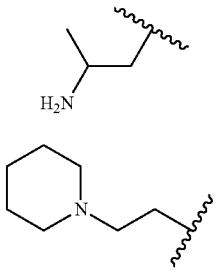 X32
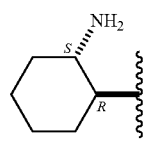 X34
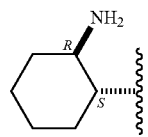 X36
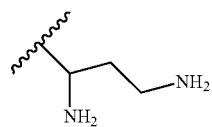 X37
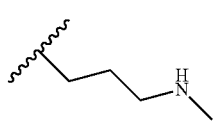 X38
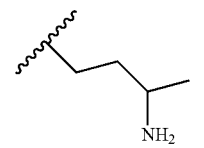 X39
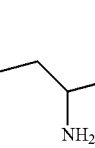 X40
-continued
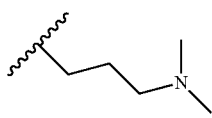 X41
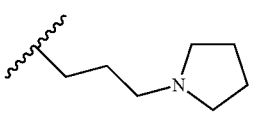 X42
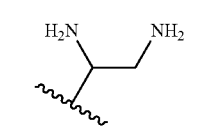 X43
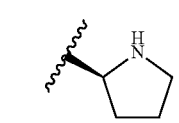 X44
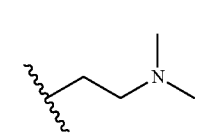 X45
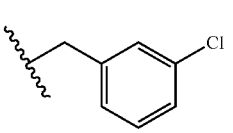 X46
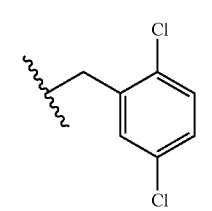 X47
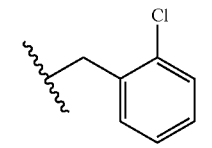 X48
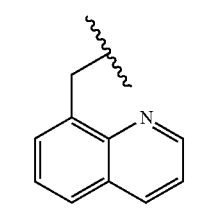 X49
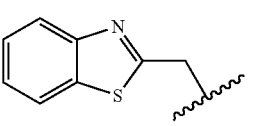 X50

X51
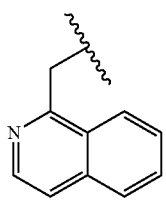

X52
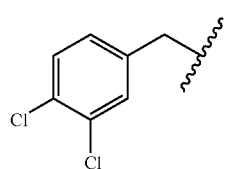

X53
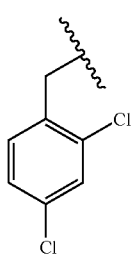

X54
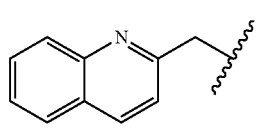

X56
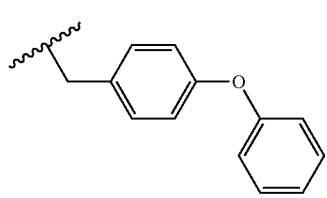

X55
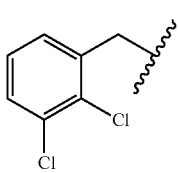

Scaffold A
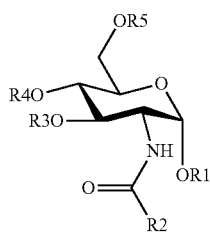

Scaffold B
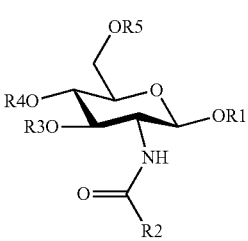

Scaffold C
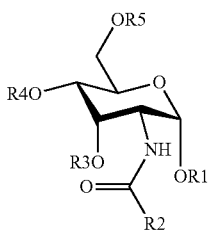

Scaffold D
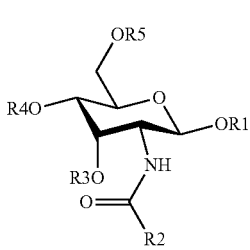

Scaffold E
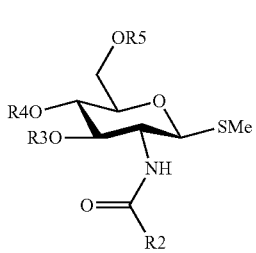

Scaffold F
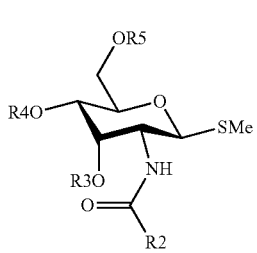

Scaffold G
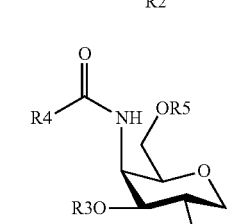

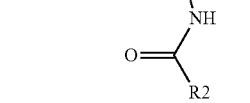

Throughout the specification and the claims (if present), unless the context requires otherwise, the term "comprise", or variations such as "comprises" or "comprising", will be understood to apply the inclusion of the stated integer or group of integers but not the exclusion of any other integer or group of integers.

Throughout the specification and claims (if present), unless the context requires otherwise, the term "substantially" or "about" will be understood to not be limited to the value for the range qualified by the terms.

It should be appreciated that various other changes and modifications can be made to any embodiment described without departing from the spirit and scope of the invention.

REFERENCES

[1] Patel, Y. C. (1999) Somatostatin and its receptor family. *Front. Neuroendocr.* 20, 157-198
[2] Csaba, Z. and Dournaud, P. (2001) Cellular biology of somatostatin receptors. *Neuropeptides* 35, 1-23
[3] T. Reisine, T. (1995) Somatostatin receptors: *Am. J. Pysiol. (Gastrointest. Liver Physiol.* 32) 269, G813-G820
[4] Bauer, W. et al. (1982) SMS201-995: A very potent and selective octapeptide analogue of somatostatin with prolonged action. *Life Sci.* 31, 1133-1140
[5] Lamberts, S. W. J. et al. (1996) Drug therapy: Octreotide. *N. Eng. J. Med.* 334, 246-254
[6] Robinson, C. and Castaner, J. (1994) Lanreotide acetate. *Drugs Future* 19, 992-999
[7] Reisine, T. and Bell. G. I. (1995) Molecular biology of somatostatin receptors. *Endocr. Rev.* 16, 427-442

The invention claimed is:

1. A method of identifying biologically active compounds comprising:
   (a) designing a first library of compounds of formula 1 to scan molecular diversity wherein for each compound of the first library $R_2$ and one of $R_1$, $R_3$, $R_4$, and $R_5$ as defined below are pharmacophoric groups and the remainder of $R_1$, $R_3$, $R_4$, and $R_5$ are non-pharmacophoric groups;
   (b) assessing the first library of compounds in one or more biological activity assay(s); and
   (c) designing a second library wherein for each compound of the second library the substituents $R_1$ to $R_5$ comprise the two pharmacophoric groups identified in step (b) and a third pharmacophoric group, and wherein the remainder of $R_1$, $R_3$, $R_4$, and $R_5$ are non-pharmacophoric groups,
such that the/each component of the first and second library is a compound of formula 1:

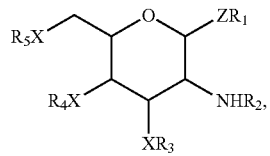

Formula 1 wherein
Z is sulphur, oxygen, NH, $NR^A$ or hydrogen, in the case where Z is hydrogen then $R_1$ is not present;
$R^A$ is selected from the set defined for $R_1$, $R_3$, $R_4$, and $R_5$, or wherein Z and $R_1$ together form a heterocycle;
X is oxygen or nitrogen;
$R_2$ is a pharmacophoric group independently selected from the group consisting of $C_2$ to $C_{20}$ alkyl, $C_2$ to $C_{20}$ acyl, wherein said acyl is not acetyl; $C_2$ to $C_{20}$ alkenyl, $C_2$ to $C_{20}$ alkynyl, $C_2$ to $C_{20}$ heteroalkyl, $C_5$ to $C_{20}$ aryl, $C_5$ to $C_{20}$ heteroaryl, $C_5$ to $C_{20}$ arylalkyl and $C_5$ to $C_{20}$ heteroarylalkyl, which is optionally substituted, and can be branched or linear, or wherein NH and $R_2$ combine to form a heterocycle;
$R_1$, $R_3$, $R_4$, and $R_5$ are each independently selected from
   (i) non-pharmacophoric groups consisting of H, methyl and acetyl, and
   (ii) pharmacophoric groups independently selected from the group consisting of $C_2$ to $C_{20}$ alkyl, $C_2$ to $C_{20}$ acyl, wherein said acyl is not acetyl; $C_2$ to $C_{20}$ alkenyl, $C_2$ to $C_{20}$ alkynyl, $C_2$ to $C_{20}$ heteroalkyl; $C_5$ to $C_{20}$ aryl, $C_5$ to $C_{20}$ heteroaryl, $C_5$ to $C_{20}$ arylalkyl and $C_5$ to $C_{20}$ heteroarylalkyl, which is optionally substituted, and can be branched or linear, or wherein X and the corresponding R moiety, $R_3$ to $R_5$ respectively, combine to form a heterocycle, and
wherein the optional substituent of each of $R_2$ and, when present as a pharmacophoric group $R_1$, $R_3$, $R_4$, and $R_5$, are selected from the group consisting of OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, aryl, cycloalkyl, heteroalkyl, heteroaryl, aminoalkyl, aminodialkyl, aminotrialkyl, aminoacyl, carbonyl, imine, sulfate, sulfonamide, phosphate, phosphoramide, hydrazide, hydroxamate, hydroxamic acid, heteroaryloxy, aminoaryl, aminoheteroaryl, thioalkyl, thioaryl and thioheteroaryl.

2. The method according to claim 1, wherein Z is sulphur or oxygen.

3. The method according to claim 1, wherein at least one of the pharmacophoric groups is selected from the group consisting of aryl, arylalkyl, heteroaryl, heteroarylalkyl and acyl.

4. The method according to claim 1, wherein the/each component of each of the libraries is a compound selected from a compound of formula 2 or formula 3 or formula 4:

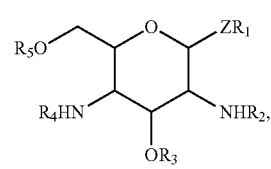

Formula 2

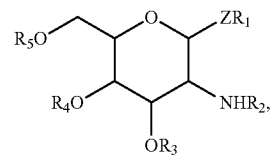

Formula 3

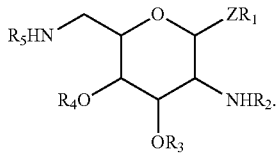

Formula 4

5. The method according to claim 1, wherein the/each compound of the first library is of the gluco- or galacto-configuration.

6. The method according to claim 4, wherein the/each compound of the second library is of the gluco- or galacto- or allo-configuration.

7. The method according to claim 6, wherein the/each compound of the second library is of the gluco-configuration.

8. The method according to claim 6, wherein the/each compound of the second library is of the allo-configuration.

9. The method according to claim 6, wherein the/each compound of the second library is of the galacto-configuration.

10. The method according to claim 1, wherein the biological assays involve peptide ligand class of GPCRs.

11. The method according to claim 1, wherein NH and $R_2$ combine to form a heterocycle.

12. The method according to claim 11, wherein the heterocycle is heteroaryl.

13. The method according to claim 11, wherein the heterocycle is selected from group consisting of triazoles, benzimidazoles, benzimidazolone, benzimidazolothione, imidazole, hydantoine, thiohydantoine and purine.

14. The method according to claim 1, wherein in the first library one pharmacophoric group comprises a positive charge and one pharmacophoric group is selected from the group consisting of aryl, heteroaryl, arylalkyl and heteroarylalkyl.

15. The method according to claim 1, wherein the method further comprises the steps of
(d) assaying the second library of compounds in one or more biological assay(s); and
(e) designing a third library wherein for each compound of the third library the substituents $R_1$ to $R_5$ comprise the three active pharmacophoric groups identified in step (c) and a fourth pharmacophoric group, and wherein each component of the third library is a compound of formula 1.

16. The method according to claim 1, wherein in each library when X is oxygen, $R_1$, $R_3$, $R_4$ and $R_5$ are each independently selected from
(i) non-pharmacophoric groups consisting of H, and methyl, and
(ii) pharmacophoric groups independently selected from the group consisting of $C_2$ to $C_{20}$ alkyl, $C_2$ to $C_{20}$ alkenyl, $C_2$ to $C_{20}$ alkynyl, $C_2$ to $C_{20}$ heteroalkyl, $C_5$ to $C_{20}$ aryl, $C_5$ to $C_{20}$ heteroaryl, $C_5$ to $C_{20}$ arylalkyl, and $C_5$ to $C_{20}$ heteroarylalkyl, which is optionally substituted, and can be branched or linear; and,
when X is nitrogen, $R_1$, $R_3$, $R_4$ and $R_5$ are each independently selected from
(i) a non-pharmacophoric group which is acetyl, and
(ii) pharmacophoric groups independently selected from the group consisting of $C_2$ to $C_{20}$ alkyl, $C_2$ to $C_{20}$ acyl wherein said acyl is not acetyl; $C_2$ to $C_{20}$ alkenyl, $C_2$ to $C_{20}$ alkynyl, $C_2$ to $C_{20}$ heteroalkyl, $C_5$ to $C_{20}$ aryl, $C_5$ to $C_{20}$ heteroaryl, $C_5$ to $C_{20}$ arylalkyl, and $C_5$ to $C_{20}$ heteroarylalkyl, which is optionally substituted, and can be branched or linear.

17. The method according to claim 16, wherein Z is sulphur or oxygen.

18. The method according to claim 16, wherein the/each component of each of the libraries is a compound selected from a compound of formula 2 or formula 3 or formula 4:

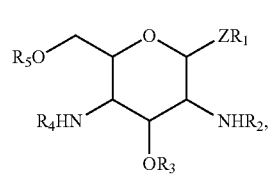

Formula 2

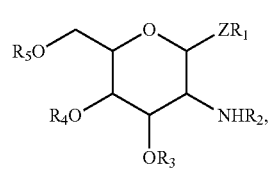

Formula 3

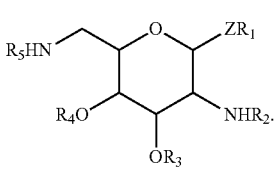

Formula 4

19. The method according to claim 17, wherein the/each compound of the second library is of the gluco- or galacto- or allo-configuration.

20. The method according to claim 16, wherein the/each compound of the first library is of the gluco- or galacto-configuration.

21. The method according to claim 16, wherein in the first library one pharmacophoric group comprises a positive charge and one pharmacophoric group is selected from the group consisting of aryl, heteroaryl, arylalkyl and heteroarylalkyl.

* * * * *